United States Patent [19]
Nobles et al.

[11] Patent Number: 5,860,990
[45] Date of Patent: *Jan. 19, 1999

[54] METHOD AND APPARATUS FOR SUTURING

[75] Inventors: Anthony A. Nobles, Huntington Beach; Charles L. Jech, Tustin, both of Calif.

[73] Assignee: NR Medical, Inc., Fountain Valley, Calif.

Related U.S. Application Data

[60] Provisional application No. 60/002,769 Aug. 24, 1995.

[21] Appl. No.: 702,315

[22] Filed: Aug. 23, 1996

[51] Int. Cl.⁶ .................................................. A61B 17/04
[52] U.S. Cl. ......................... 606/144; 606/139; 606/147
[58] Field of Search .................................. 606/144, 145, 606/146, 143, 139

[56] References Cited

U.S. PATENT DOCUMENTS

| | | |
|---|---|---|
| 5,059,201 | 10/1991 | Asnis . |
| 5,304,184 | 4/1994 | Hathaway et al. . |
| 5,374,275 | 12/1994 | Bradley et al. .......................... 606/144 |
| 5,403,329 | 4/1995 | Hinchcliffe .............................. 606/139 |
| 5,458,609 | 10/1995 | Gordon et al. .......................... 606/144 |
| 5,462,560 | 10/1995 | Stevens .................................... 606/144 |
| 5,470,338 | 11/1995 | Whitfield et al. ....................... 606/144 |
| 5,527,321 | 6/1996 | Hinchliffe ................................ 606/139 |
| 5,573,540 | 11/1996 | Yoon ....................................... 606/139 |

*Primary Examiner*—Gary Jackson
*Attorney, Agent, or Firm*—Knobbe, Martens, Olson & Bear, LLP

[57] ABSTRACT

A suturing device capable of suturing biological tissue including the walls of arterial blood vessels comprises suture clasps for insertion inside the central passage way of an arterial vessel. The device utilizes a suture introducer housing to aid insertion of the suture clasps in the vessel. A suture catch operates to catch a suture held by the suture clasps, remove the suture from the suture clasps, and pull the suture through the arterial wall, so the suture can be completed.

28 Claims, 24 Drawing Sheets

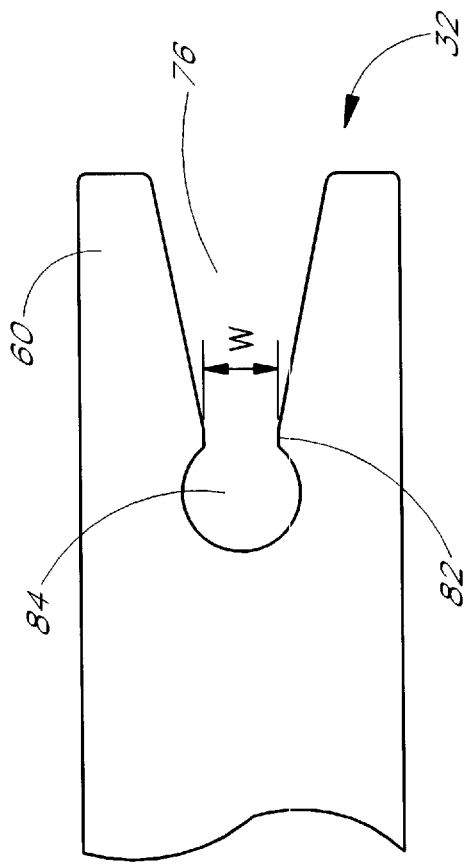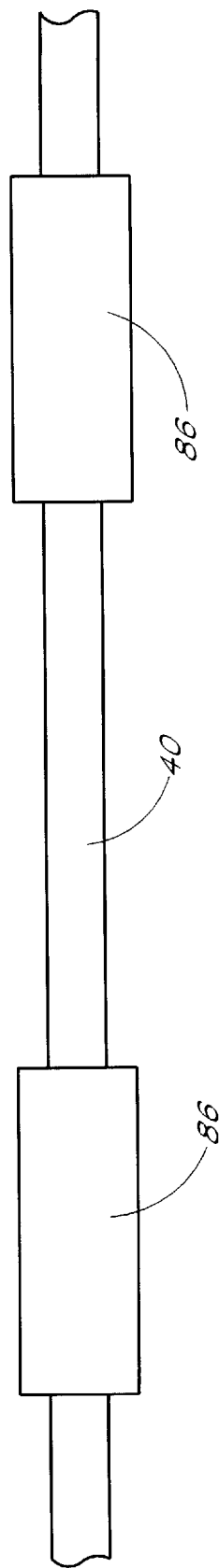
FIG. 6
FIG. 7

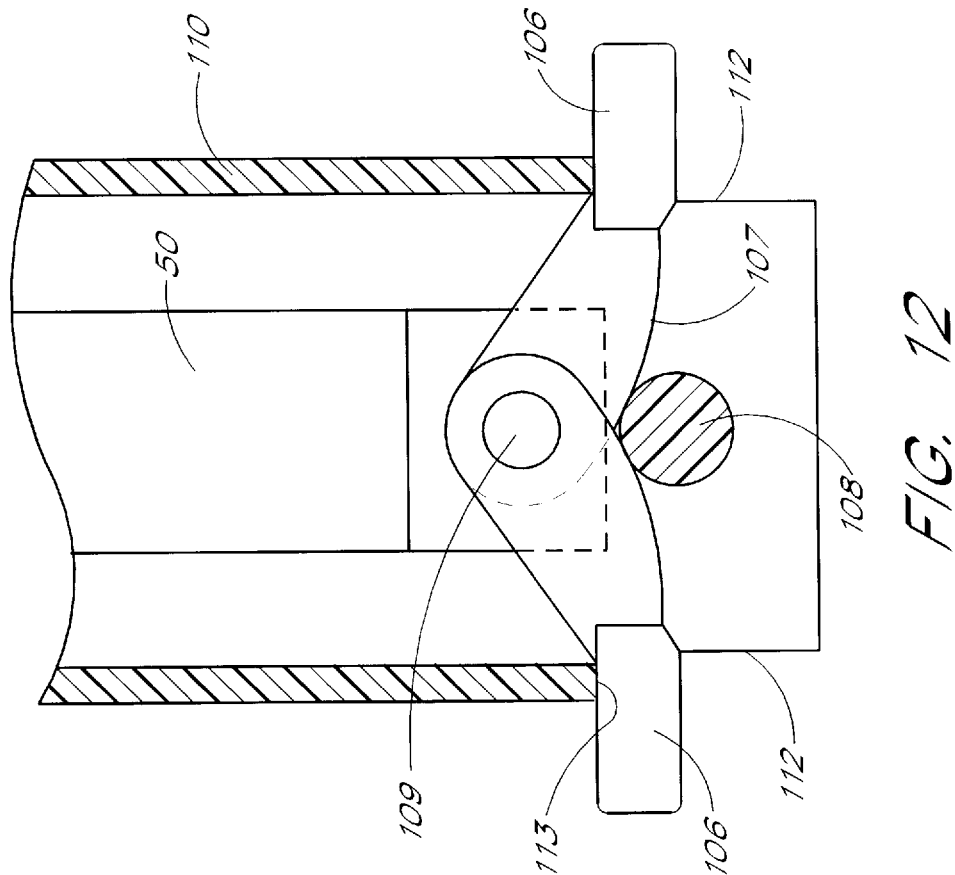
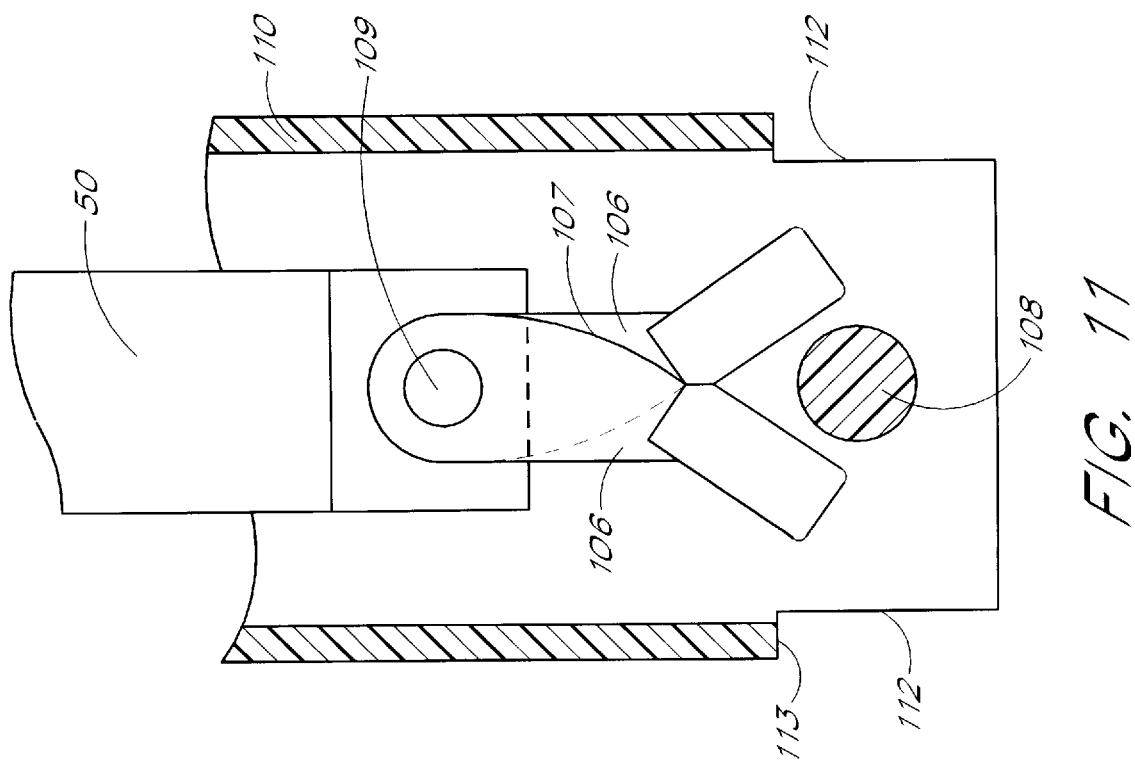

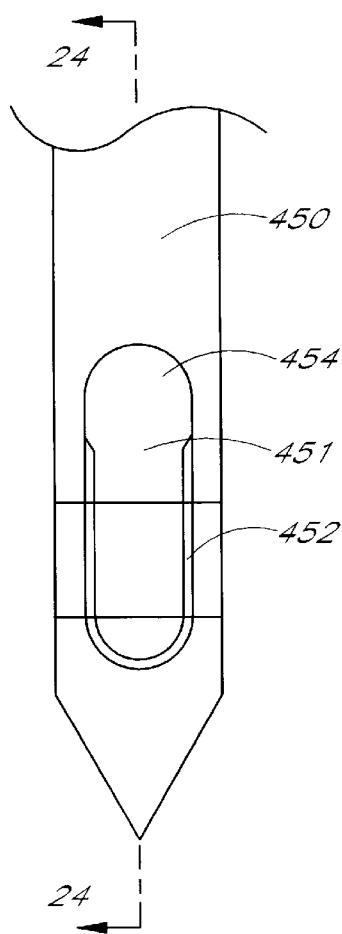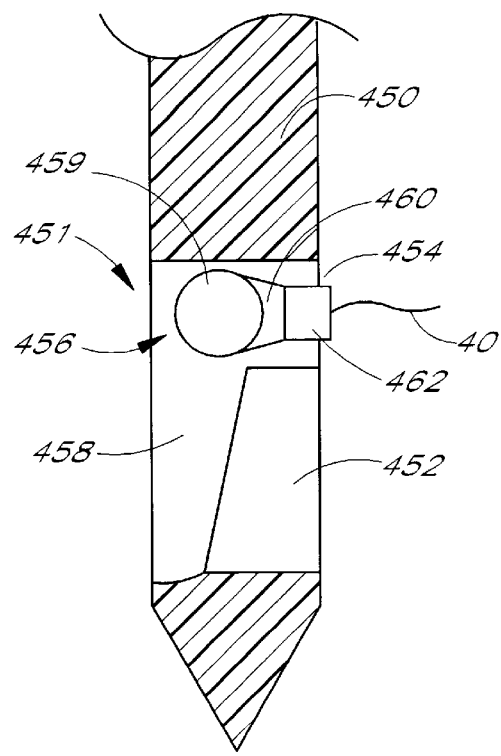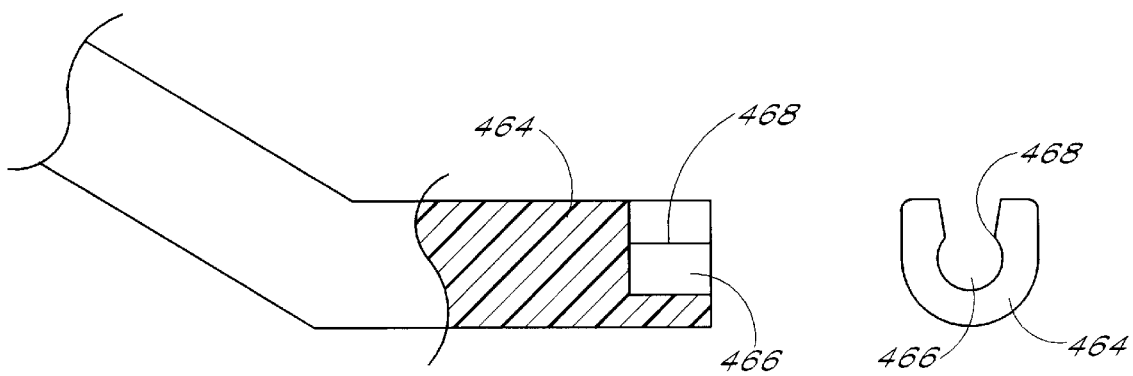

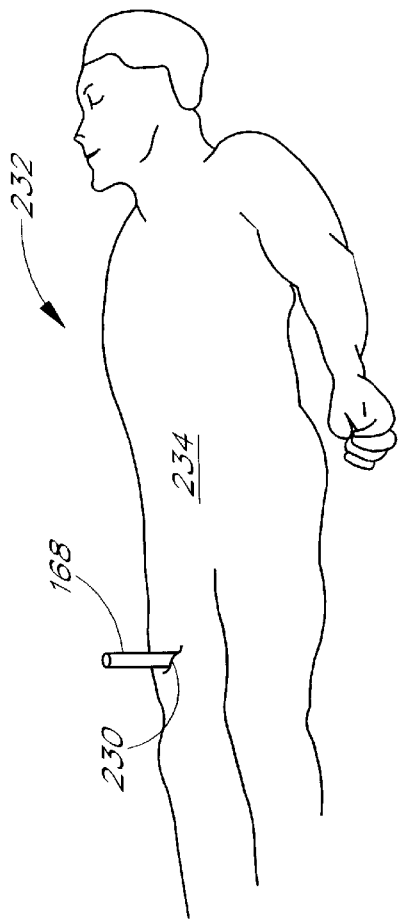
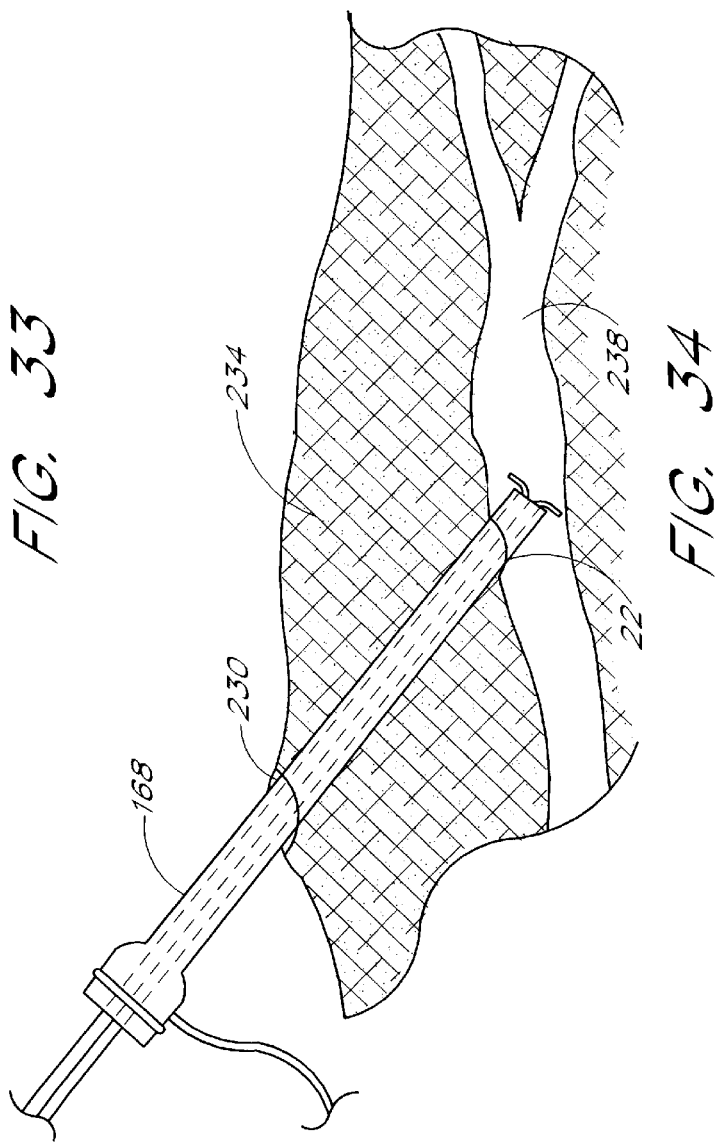
FIG. 33
FIG. 34

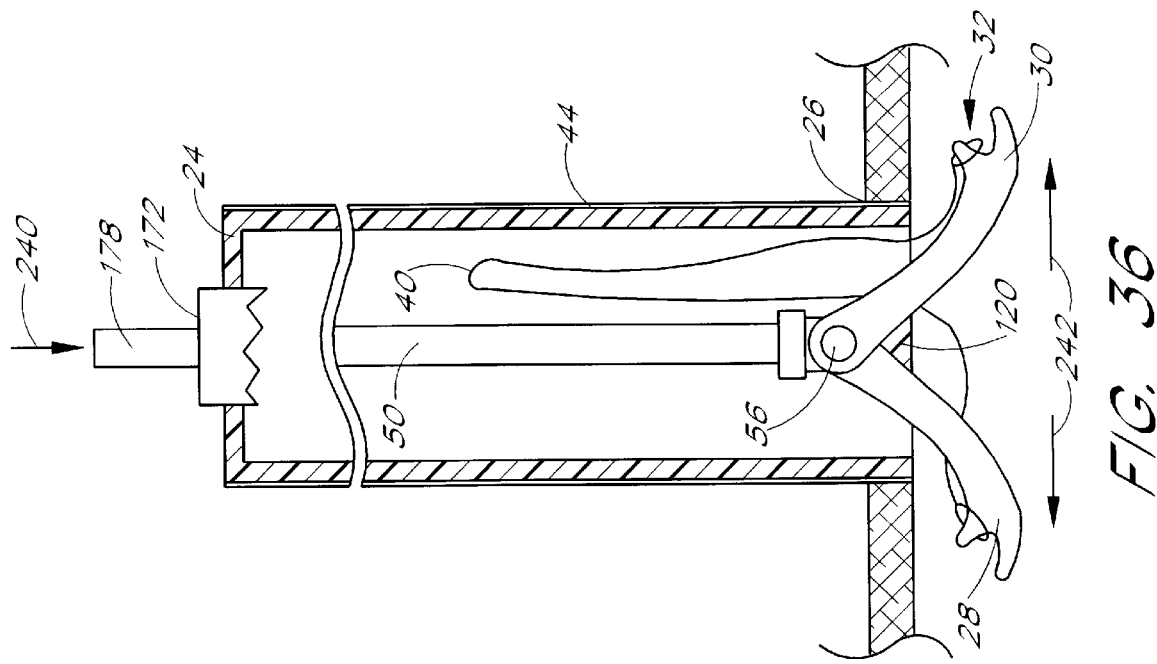
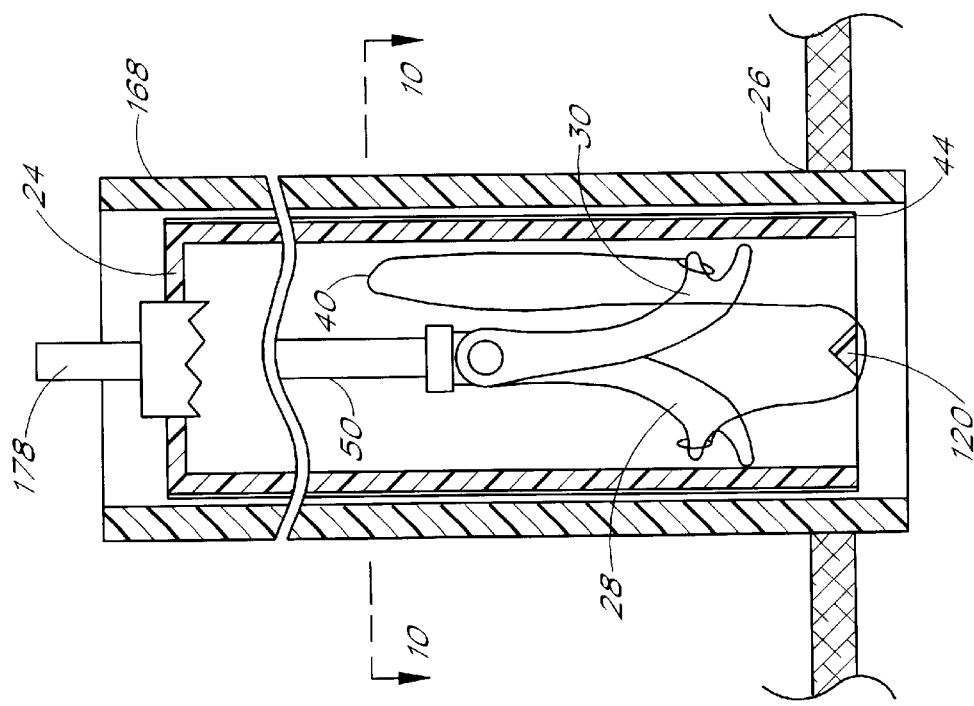

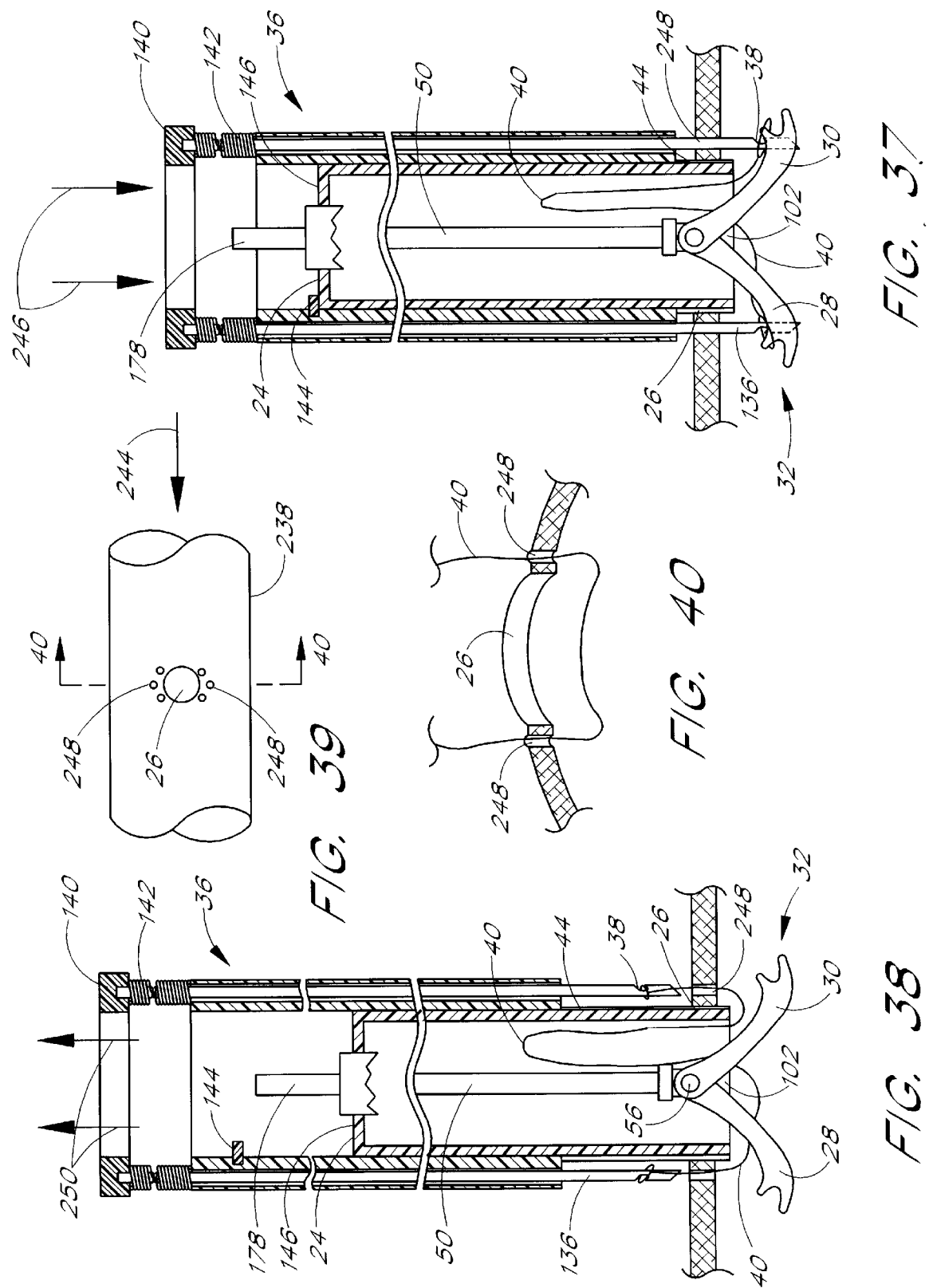

METHOD AND APPARATUS FOR SUTURING

RELATED APPLICATIONS

This application claims the benefit of U.S. Provisional application Ser. No. 60/002,769 filed Aug. 24, 1995.

BACKGROUND OF THE INVENTION

This invention relates to suturing devices and suturing methods.

Health practitioners frequently use sutures to close various openings such as cuts, punctures, and incisions in various places in the human body. Because of their importance and frequent use, several types of sutures and devices for their implantation and extraction have been developed. These devices include needles having various shapes and sizes as well as devices for inserting and removing staples. Generally, sutures are convenient to use and function properly to hold openings in biological tissue closed thereby aiding in blood clotting, healing, and prevention of scaring. There are however some circumstances under which it is not feasible to use conventional sutures and suturing methods to close an opening. Some of these circumstances occur with incisions in arterial walls.

The arteries are the blood vessels which carry blood to the various body cells from the heart, and compared to veins, which carry blood back to the heart, the blood pressure in arteries is significantly higher. A typical blood pressure in the veins is 30 mmHg. A typical arterial blood pressure measurement is 120 over 80 mmHg. The higher reading, 120 mmHg, represents the systolic pressure which occurs when the ventricles of the heart contract forcing blood into the arteries, and the lower reading, 80 mmHg, represents the diasystolic pressure when the ventricles of the heart are relaxed and refilling with blood.

During a typical arterial catheterization procedure, which can be performed in a hospital or catheterization lab, a relatively small incision is made in the upper thigh and then in the femoral artery. A catheter is inserted through the incision and directed along an arterial path to a target area such as the heart for performance of any number of many possible procedures such as angioplasty and angiograms. Upon completion of the catheterization procedure, closure of the arterial incision is problematic because of the relatively high blood pressure in the arteries and because the small incision made in the thigh does not provide enough working space for a health practitioner to suture the artery in a conventional manner with hemostats and conventional suturing needles.

To close the incision in the femoral artery and prevent significant blood loss, the catheter is removed, and a health practitioner applies direct pressure to the leg for twenty minutes carefully monitoring the femoral pulse to assure that the applied pressure is not compressing the artery to the point of blockage (occlusion). The health practitioner applies the pressure immediately after the procedure because the artery must not be occluded or severe injury could result to the leg. After twenty minutes, the health practitioner will give this responsibility to another person typically a nurse who will continue to monitor the application of direct pressure for an extended period of time typically beyond twenty-four(24) hours.

Because it is not possible for medical personnel to personally apply direct pressure for such a long time, several devices have been developed to aide in application of direct pressure to the thigh. These devices include large clamps, sand bags and others, yet because of the high blood pressure in the artery, the blood clots on the artery frequently rupture while the direct pressure devices are applied or after direct pressure is removed. If a blood clot ruptures and is not restored, the patient may bleed to death. Because blood clots on the artery frequently rupture and because of the possible severe consequences of a ruptured blood clot, patients are held overnight in the hospital or catheterization lab for observation to assure that the blood clots do not rupture. Thus, these types of procedures are performed on an inpatient basis, so that the patient is observed long enough after the procedure to assure that the clot is permanently established and the femoral artery is not bleeding.

If during the observational period the direct pressure repeatedly fails to close the vessel, a health practitioner may have to operate on the patient. During this operation, the patient is anesthetized, the blood flow to the artery is occluded, an incision is made in the upper thigh to allow enough room for conventional suturing with a needle, the artery is sutured, the blood flow restored, and the incision in the thigh is sutured. This obviously results in additional discomfort to the patient, a longer hospital stay, and increased expense.

Thus, reducing the time which direct pressure must be applied to an arterial opening, the frequency with which blood clots on arteries rupture, the time which must be spent in the hospital or catheter lab, and the frequency of operations are desirable to reduce medical costs and patient discomfort.

SUMMARY OF THE INVENTION

There is, therefore, provided in the practice of the invention a novel suturing device for suturing that is particularly useful in suturing an opening in a vessel wall although other tissue may be sutured as well. The device comprises at least one suture clasp for holding a suture and at least one suture catch operatively positioned relative to the suture clasp.

In a preferred embodiment the device is provided with a tube having an aperture and at least one arm having a first retracted position inside the tube and a second deployed position outside the tube. The suture clasp is attached to the arm. An actuating rod extends to the aperture and attaches to the arm at one end and at the other end to an arm actuator assembly or an arm deployment handle. The arm comprises a Y-shape having a suture catch receiving area and is pivotally attached to the actuating rod in one embodiment. In another embodiment, the arms are fixably attached to the actuating rod and comprise at least one resilient arm having an at rest shape corresponding to the desired deployed position.

The suture clasp comprises at least one aperture adapted to receive a cylindrical band crimped on to a suture. The aperture is preferably key-holed shaped and extends to an edge of the clasp, so that the cylindrical band snaps into the aperture. In an alternate embodiment, the suture clasp comprises a pair of tips each having an outside edge defining an indentation for receiving a knot or bead which is on a suture. This embodiment can further comprise a resilient member attached to each of the tips so that tension in the resilient member helps hold the suture.

A suture catch assembly is preferably provided with at least one suture catch. In this embodiment the suture catch preferably comprises an upwardly angled slot near the sharp end of a needle. For use with this suture catch, the suture clasp comprises an arm defining a suture catch receiving area.

In an alternate embodiment, the suture catch comprises an aperture for receiving a suture fitting. In this embodiment, the suture catch comprises a needle defining a slot having a top with a peg inside the slot extending downwardly from the top. The peg is movably to receive the suture fitting into the slot and lock it therein. The suture catch assembly further comprises an activation ring attached to at least one needle. The activation rings provide with a stop the control of depth of entry of the suture catch.

In another alternate embodiment, the suturing device comprises a plurality of arms extending a plurality of directions. Each arm has a suture clasp for holding at least one suture. A penetrating mechanism is provided operably positioned relative to the suture clasp to penetrate biological tissue with at least one suture.

In one embodiment the penetrating mechanism comprises at least one suture clasp, and a circumferential suture catch can be provided to catch the suture. A suture introducer housing is provided with a spreader located in an aperture of the housing. The spreader extends across the diameter line of the housing and is substantially perpendicular to the longitudinal axis of the housing. The spreader operates to evenly spread the arms. The spreader can comprise a substantial triangular bar, a cam pin, or a pivot shaft spreader.

The suture clasp arms comprise, in an alternate embodiment, an upper lever arm and a lower pivot arm having the suture clasp thereon. An actuating rod having a distal end attached to the arm also has a proximal end attached to a three-sector arm actuator assembly. The arm actuator assembly comprises an actuation post having a height corresponding to the depressed height of the activation ring such that the actuation post is depressed simultaneously with the activation ring. In an alternate embodiment the actuating rod is severable so that a detachable arm deployment handle is removeably attached the proximal end of the actuating rod.

There is therefore provided in the practice of this invention a novel method for suturing. The method comprises holding a suture with at least one suture clasp and introducing the suture held by the suture clasp into an area to be sutured. The surrounding tissue is then penetrated and the sutures tied.

There is also provided a novel method for suturing a vessel. The method comprises holding a suture with at least one suture clasp and introducing the suture held by the suture clasp into an internal passage of the vessel. The vessel walls are then penetrated and the suture tied.

In a preferred method, penetrating the vessel wall comprises piercing the vessel wall with a suture clasp. Alternatively, penetrating the vessel wall comprises piercing the vessel wall with a suture catch. The suture catch is used to catch the suture from the suture clasp and retract it from the vessel wall.

Initially, a suture introducer housing is introduced into the vessel wall, and the suture is introduced into the vessel through the suture introducer housing. The method further comprises positioning the suture beyond an outer diameter of the housing and penetrating the vessel wall outside the outer diameter of the housing. Preferably the suture is positioned with portions of the suture on opposite sides of the opening and the suture extending in a direction transverse to the flow of blood through the vessel.

In an alternate embodiment, the suture introducer housing is introduced into the passage way of a vessel through an introducer. This alternate embodiment comprises deploying the suture clasp beyond the outer diameter of the tube and removing the introducer. A suture catch assembly is then pushed over the housing up to the vessel wall. Alternatively, the introducer is left in place, and a suture catch assembly having an aperture, a slit, and a suture catch, is placed over the introducer. In an alternate embodiment, the method further comprises attaching an arm deployment handle to an actuating rod.

These and other features and advantages of the present invention will appear from the following detailed description and the accompanying drawings in which similar reference characters denote similar elements throughout the several views.

BRIEF DESCRIPTION OF THE DRAWINGS

FIG. 6 is an enlarged elevational view of a suture clasp;

FIG. 7 is an enlarged elevational view of a suture having bands crimped thereon;

FIG. 11 is a partial cross-sectional view of an alternate embodiment for deploying the arms;

FIG. 12 is a partial cross-sectional view of the embodiment of FIG. 11 with the arms deployed;

FIG. 23 is a rear elevational view of a needle tip having still another alternate embodiment of the suture catch;

FIG. 24 is a cross-sectional view of the needle tip of FIG. 23 taken along line 24—24 of FIG. 23;

FIG. 25 is a partial cross-sectional side view of an alternate embodiment of a suture clasp arm to hold a suture fitting;

FIG. 26 is an end view of the suture clasp arm of FIG. 25;

FIG. 33 is a schematic perspective view illustrating the preferred application of the present invention;

FIG. 34 is a schematic internal view of a human thigh illustrating the application of the invention shown in FIG. 33;

FIG. 35 is a partial cross-sectional view of the suture introducer housing of FIG. 1 with the introducer over the housing;

FIG. 36 is a partial cross-sectional view of the suture introducer housing of FIG. 1 with the suture clasp arms deployed;

FIG. 37 is a partial cross-sectional view of the suture introducer housing and suture catch assembly of FIG. 1 illustrating the operation of the suture catch assembly;

FIG. 38 is a partial cross-sectional view of the suture introducer housing and the suture catch assembly of FIG. 1 illustrating penetrating the vessel wall with a suture;

FIG. 39 is a schematic view of a vessel illustrating the location of the suture;

FIG. 40 is a schematic cross-sectional view taken along line 40—40 of FIG. 39.

DETAILED DESCRIPTION

Figure 1:
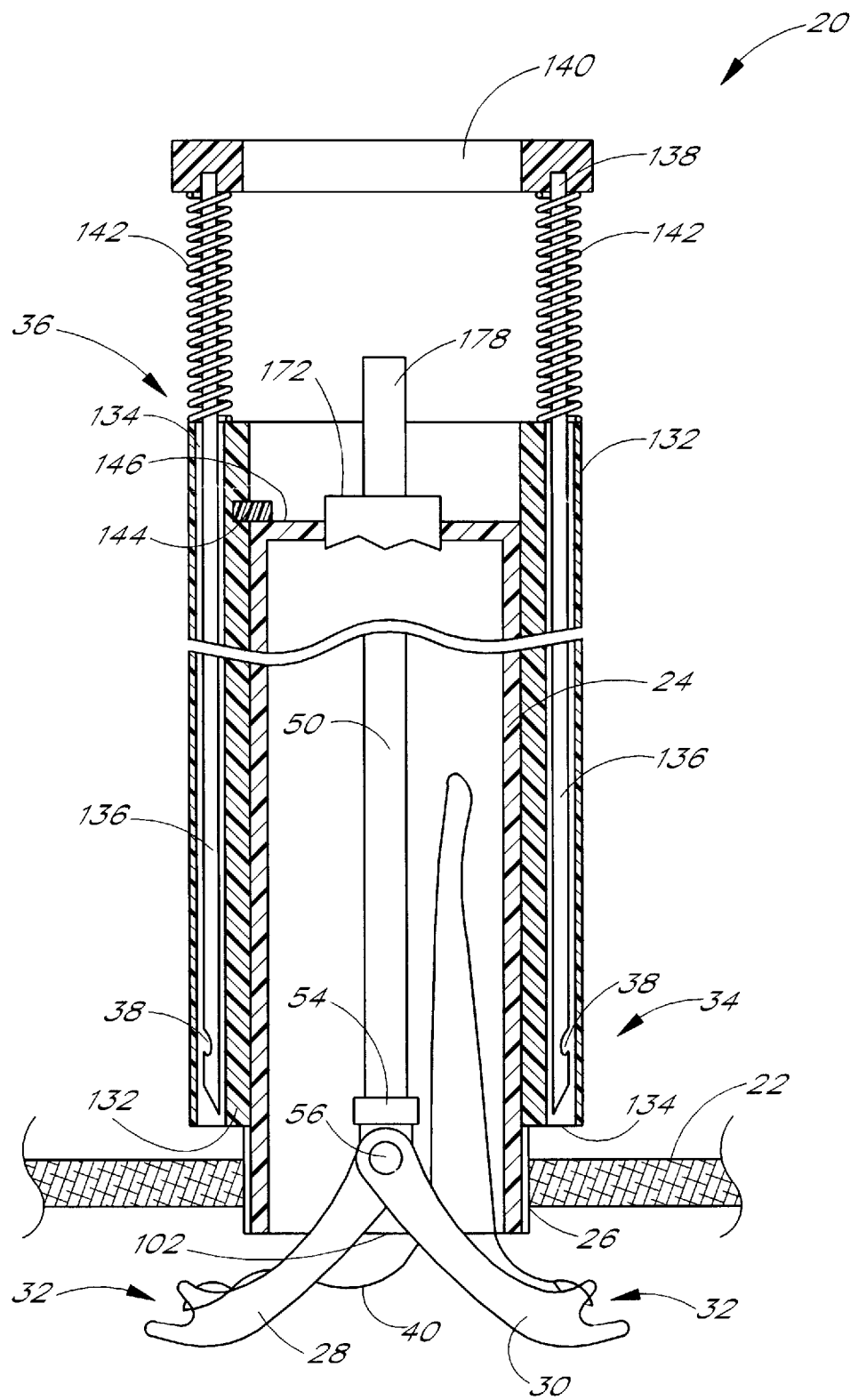
FIG. 1 is a partial cross-sectional view of a suturing device according to the present invention having a suture catch assembly and a suture introducer housing.

FIG. 1 shows a suturing device, generally designated 20, for suturing vessel walls and other biological tissue. Preferably, the device is for use in suturing arterial vessel walls 22 in which it was previously not feasible to place sutures because of the small incision or cut in surrounding tissue. However, the device could be used to suture other tissue such as a patent ductus arteriosus, a patent foramen ovale, a heart defect, a puncture wound, and the like. The suturing device comprises a suture introducer housing 24 for insertion into an opening 26 in the arterial wall 22. Suture clasp arms 28, 30 are deployably housed in the housing during insertion, and after insertion into the vessel, the arms are deployed to the position shown in FIG. 1. When deployed, the suture clasp arms extend outside the circumference of the suture introducer housing. Each arm has at least one means, generally designated 32 and schematically illustrated, for clasping a suture 40. A penetrating mechanism, generally designated 34, is provided for penetrating the vessel wall 22. The penetrating mechanism is provided on either the suture introducer housing or on a suture catch assembly, generally designated 36. When, as shown in FIG. 1, the penetrating mechanism is part of the suture catch assembly 36, the penetrating mechanism also comprises a suture catch 38 for catching the suture 40 and dislodging it from the clasping means 32. The suture catch assembly operates to pull the suture held by the suture catch through the vessel wall. After the ends of the suture are pulled outside the vessel, the introducing housing can be removed and the suture tied to close the vessel.

Figure 2:
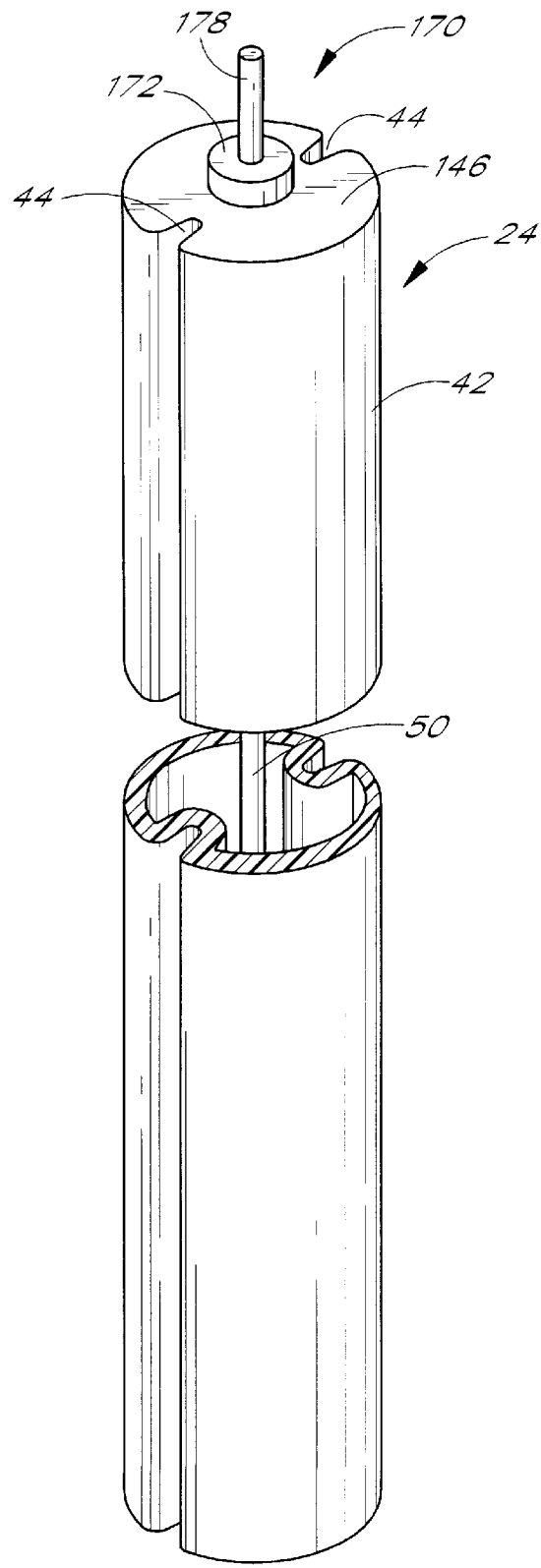
FIG. 2 is a bifurcated perspective view of the suture introducer housing of FIG. 1.

In a preferred embodiment shown in FIG. 2, the suture introducer housing 24 is a generally cylindrical and thin walled hypo tube. The term "hypo tube" is used to describe a hollow elongated cylindrical member with a thin wall such that the inner diameter and outer diameter vary by a relatively small amount in the range of few thousandths of an inch to tens of thousandths of an inch. The outer surface 42 of the housing comprises a key way groove 44 (exaggerated for clarity) to align the housing with a key 46 (FIG. 16) on the inner surface 48 of the suture catch assembly 36. An arm actuation assembly 170, to be described below, for deploying the suture clasp arms protrudes from the proximal end of the housing, and an actuating rod 50 extends from the actuation assembly through the housing to the suture clasp arms.

Referring additional back to FIG. 1, the suture clasp arms 28, 30 are attached to the distal end 54 of the actuating rod 50. In this embodiment, the arms are pivotally attached to the actuating rod and pivot around pivot shaft 56. The suture is held inside the housing and is positioned underneath the spreader 102, so that it can be removed from the entire housing. (The position of the suture is more clearly shown in FIG. 31.) The arms, which are shown in more detail in FIG. 3, terminate with the clasping means 32 (schematically illustrated). Each arm has an elongated body 58 which attaches to the pivot shaft 56 at one end and to the clasping means 32 at the other. The length of the body controls how far beyond the circumference of the suture introducer housing the arms extend when they are deployed by the actuating rod. Preferably, the arms are Y-shaped with an offset body, and there is a clasping means at each tip 60, 62 of the Y-shaped arm.

Figure 5:
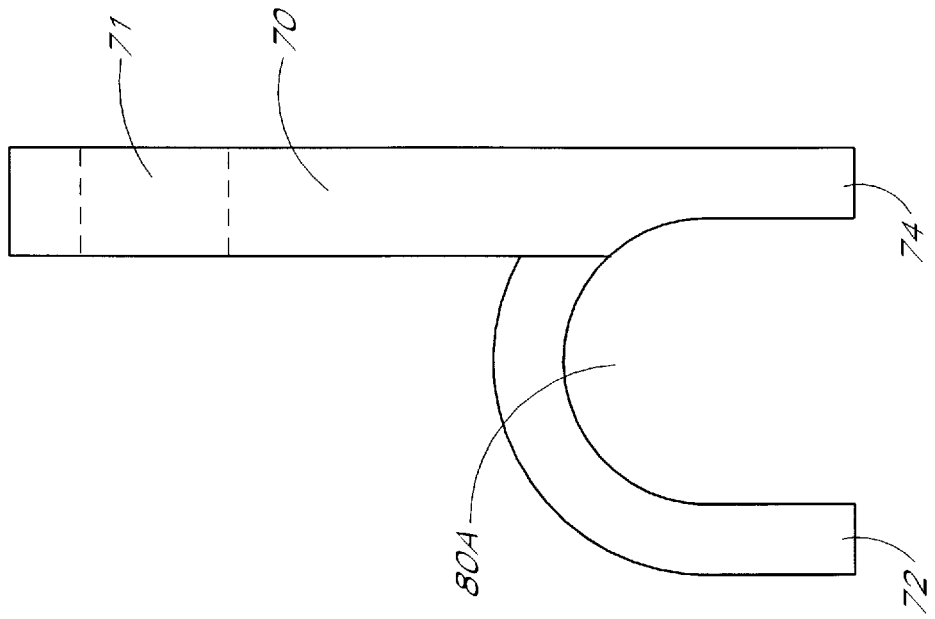
FIG. 5 is an elevational view of another alternative embodiment of the suture clasp arm.
Figure 4:
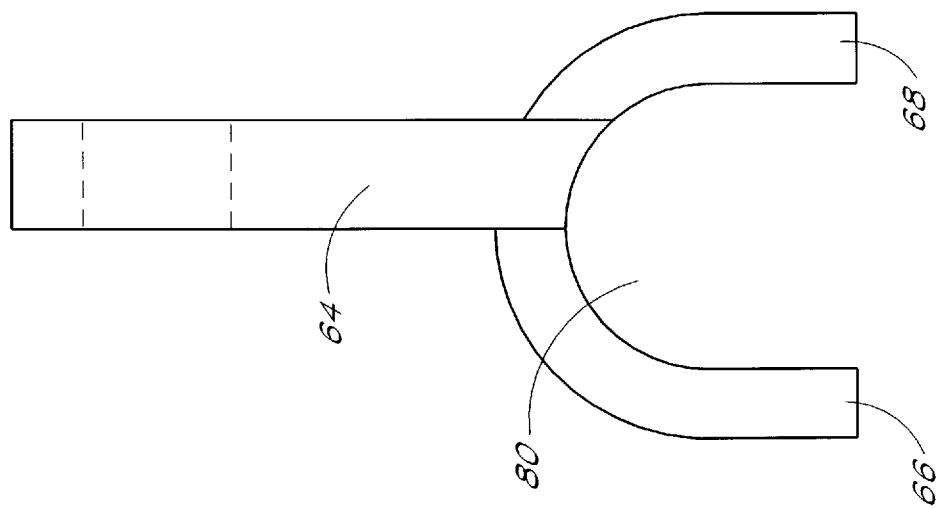
FIG. 4 is an elevational view of an alternate embodiment of the suture clasp arm.

An alternate embodiment of the arms shown in FIG. 4 more clearly shows the Y-shape with an offset body 64. The body 64 is off center form the tips 66, 68, so that a complimentary arm can pivot on the same pivot shaft without interference. Thus, the Y-shape of the arms allows the arms to pivot beside each other outwardly from and inwardly to their undeployed position without interference from the other arm. The Y-shape of the arm also provides an open area or suture catch receiving area 80 into which the suture catch fits to catch the suture. Other arm shapes such as the h-shaped arm shown in FIG. 5 provide the same benefits. The h-shaped arm has a body 70 with an aperture 71 for attachment to a pivot shaft and each tip 72, 74 of the arm is provided with a suture clasp. The body of the h-shaped arm is positioned all the way to the side of the arm and functions similarly to the Y-shaped arm. The embodiment of the suture clasp arm shown in FIG. 5 also has suture catch receiving area 80A.

Figure 3:
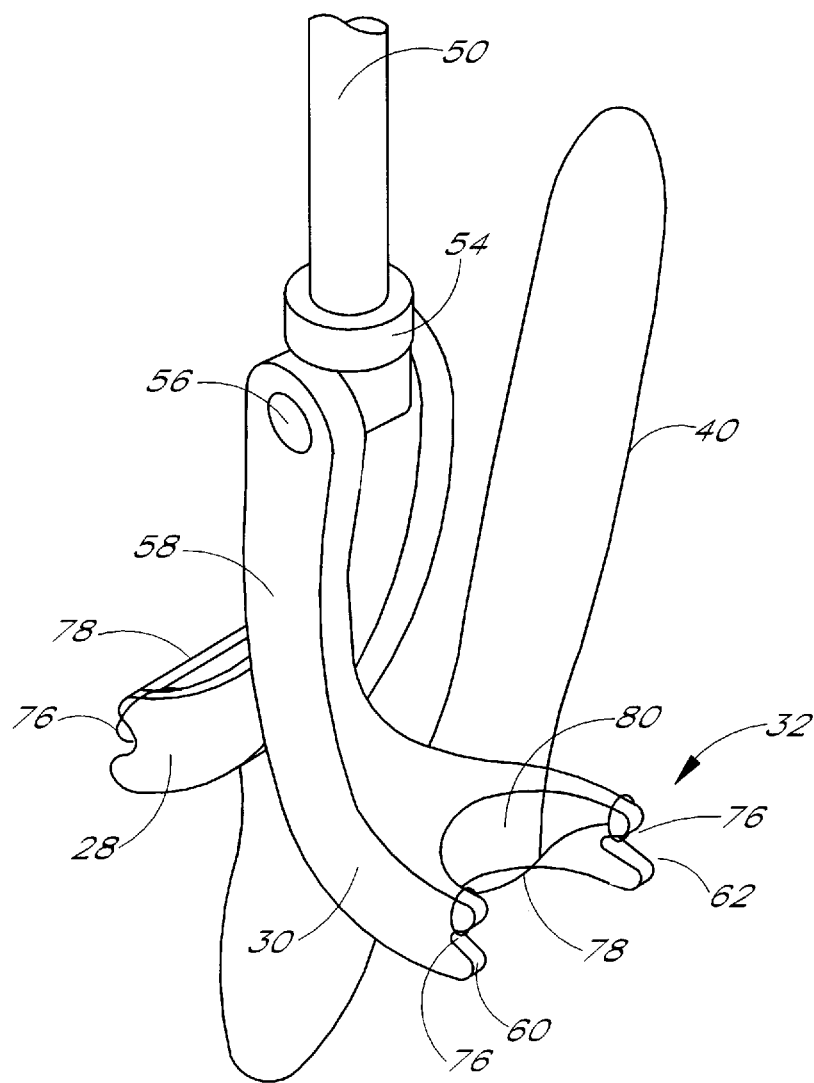
FIG. 3 is a partially schematic perspective view of the suture clasp arms of FIG. 1.

Referring to FIGS. 6 and 7 which illustrate an actual embodiment of the suture clasp 32, the suture clasp comprises a key hole shaped slot 76 which widens toward the end of the tip to receive the suture. As illustrated in FIG. 3, a loop 78 is tied in each end of the suture. The loop is sized to fit tightly between the suture clasps on each arm. The key hole shaped slot 76 is elongated and narrows away from the end of the tip 60 to a neck 82 having a width W. The end 84 of the slot is circular with a diameter greater than the neck width W. The diameter of the circular end 84 of the slot is sized to receive either the outer diameter of a suture, shown in FIG. 7, or the outer diameter of cylindrical bands 86 which are crimped onto the suture 40. The suture or the bands have an outer diameter approximately the same size as the diameter of the end of the slot but smaller than the neck width W. Because the diameter of the bands (or suture) is smaller than the width of the neck, the bands snap into the end of the slot and are securely held therein until removed by the suture catch. In an alternate embodiment (FIG. 13), it is desirable for the slots to open upwardly when they are in the deployed position, so that the suture is pulled straight up out of the slots.

Figure 8:
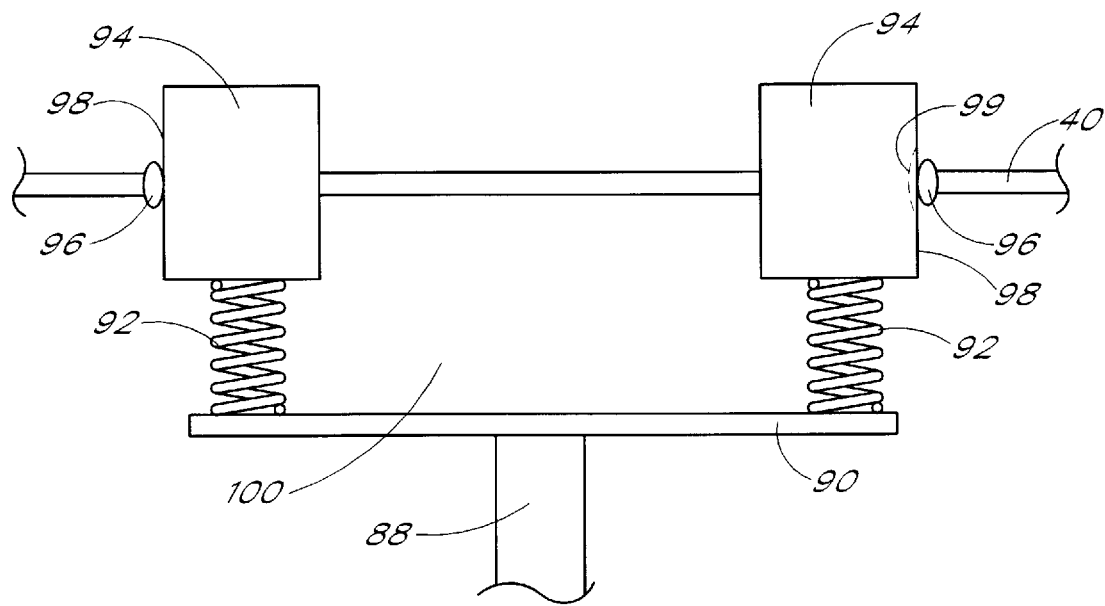
FIG. 8 is an enlarged elevational view of an alternate embodiment of a suture clasp.
Figure 9:
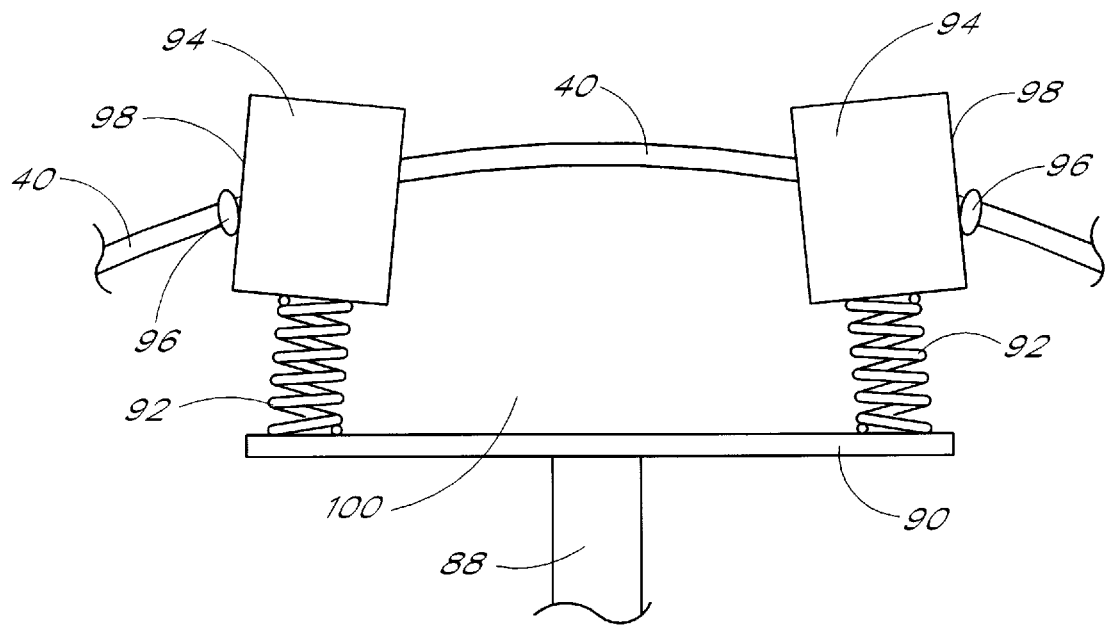
FIG. 9 is an elevational view of the suture clasp of FIG. 8 illustrating the action of the suture, and the suture clasp as the suture is being removed from the suture clasp.

Another embodiment of the suture clasp is shown in FIG. 8. In this embodiment the arm comprises a shaft 88 extending to a plate or bar 90. A resilient element 92 is attached at each end of the bar, and tips 94 are attached to the end of each resilient member. The tips have slots as previously described and shown by FIG. 6. The suture 40 has beads 96 fixed thereto or knots tied therein. The beads are spaced apart by a distance just less than the distance between the outer edges 98 of the tips 94. With this distance between the beads, the tips must be slightly bent toward each other thereby loading the resilient members to receive the suture. When the tips are pulled inwardly and the resilient members loaded, the suture is held in place by the force from the resilient members. Therefore, the suture is held in tension between the tips. When the suture catch is guided through the suture catch receiving area 100, the resilient members are further deformed as the suture is forced to make an arc to receive the suture catch as illustrated in FIG. 9. The resilient members then bend in the direction that the suture catch is retracted, so that the suture slides smoothly out of the clasp. If desired, the outer edges 98 of the tips may be indented 99 to receive and more securely hold the beads or knots on the suture.

Figure 10:
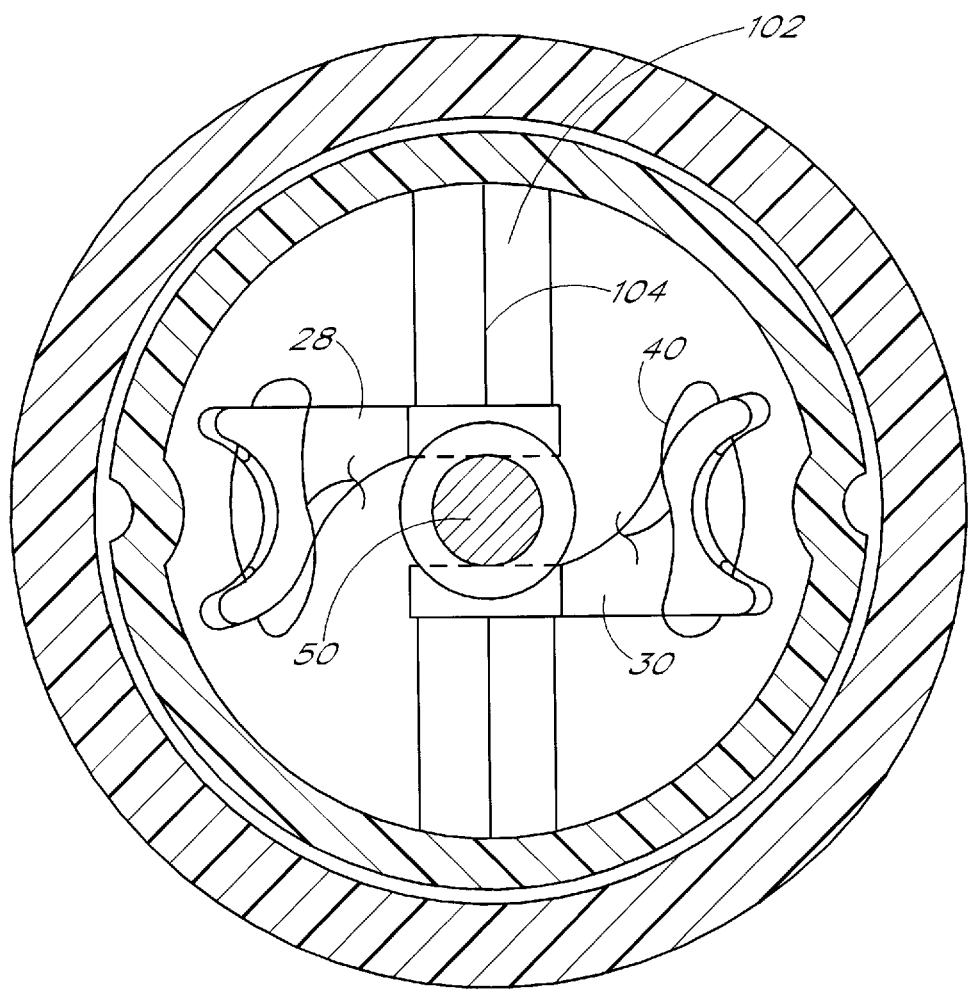
FIG. 10 is a cross-sectional view taken along line 10—10 of FIG. 31 below.

Referring back to FIG. 1, the suture clasp arms 28, 30 are deployed when the actuation rod 50 forces the arms downwardly to a triangular spreader 102 extending across a diameter line of the suture introducer housing as shown in FIG. 10. One vertex 104 of the triangle is positioned centrally in the housing and extends upwardly. The triangle is preferably isosceles with respect to the upward extending vertex 104, so that as the arms engage the spreader, pivot about the pivot shaft, are uniformly spread, and ultimately extend the same distance beyond the circumference of the housing. The surfaces of the spreader and arms which engage to deploy the arms are preferably smooth, so that the deployment of the arms is smooth.

An alternate embodiment for deploying the arms is shown in FIGS. 11 and 12. The arms 106 are pivotally attached to the actuating rod 50 with a pivot shaft 109, and a circular spreader bar 108 or cam pin extends across a diameter line of the housing 110. When the actuation rod forces the suture clasp arms to engage the circular spreader they are forced into the deployed position of FIG. 12. To obtain smooth deployment of the arms, the bottom surface 107 of the arms forms a curved camming surface for engaging the circular spreader. The housing has two slit shaped openings 112 evenly spaced around the circumference of the housing through which the arms extend into the deployed position. The end of the openings also forms a stop 113 to prevent the arms from moving past the deployed position, and with the openings in the housing, the shape of the arms is simplified. Because the arms do not have to curve down out of the housing, the arms are straighter than in the previous embodiments.

Figure 13:
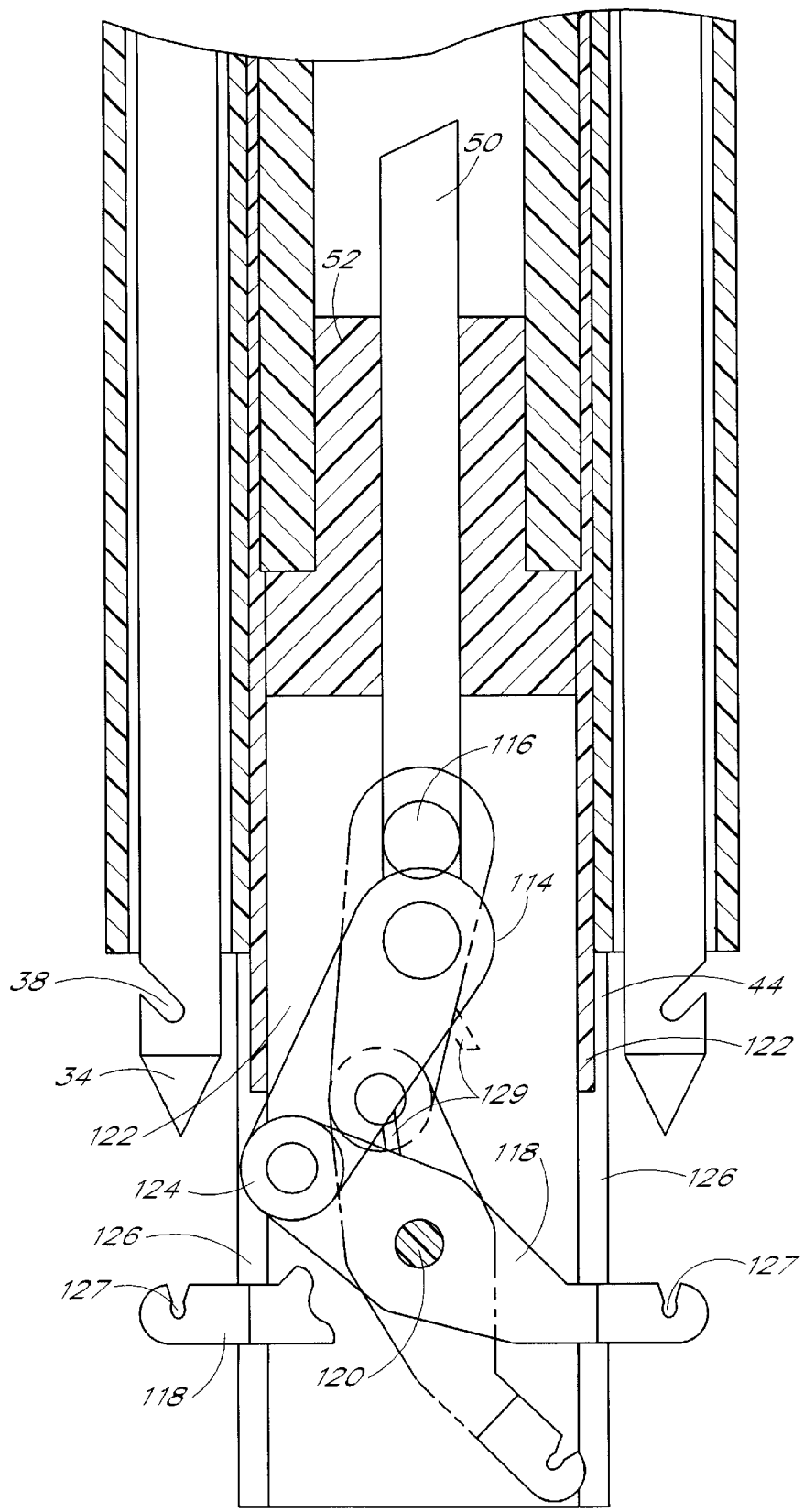
FIG. 13 is a partial cross-sectional view of still another alternate embodiment for deploying the suture clasp arms.

Another alternative means for deploying the arms is illustrated in FIG. 13. Each arm comprises an upper lever arm 114 pivotally attached at one end to the actuating rod 50 with a pivot shaft 116 and a lower pivot arm 118 pivotally attached to the other end of the upper lever arm. The lower pivot arm rotates around a pivot shaft spreader 120 which is attached to the housing 122 and extends across a diameter line of the housing. When the actuating rod 50 is forced distally farther into the housing, the lower pivot arms are forced to pivot around the pivot shaft spreader, and the arms are deployed to the position shown in solid lines. As the lower pivot arm rotates, the upper lever arm rotates relative to the pivot shaft, and the junction 124 between the upper and lower arms is translated downward (distally) and outwardly toward the circumference of the housing. When the actuating rod is retracted from the housing, the junction is moved upward and centrally in the housing, and the lower pivot arm is rotated to the retracted position shown in partial dashed lines.

The housing, similar to the embodiment of FIG. 12, has slit openings 126. The openings extend a greater distance along the length of the housing than in FIG. 12 to allow room for the lower lever arm to exit the housing and provide sufficient room for the junction to move outwardly. A stop 129 attached to the upper lever arm is placed between the upper lever arm and the lower pivot arm to prevent the arms from moving past the deployed position. Alternatively, the stop can be inherent in the lower pivot arm and upper lever arm. This would include a notch on the side of one of the arms which the other arm would contact to limit the movement of the arms.

FIG. 13 also illustrates an alternate embodiment of the suture clasp slot. The slot 127 opens upwardly toward the penetrating mechanism instead of transverse to the penetrating mechanism as in the previous embodiment. Further, FIG. 13 illustrates the use of a sealing member 52 inside the suture introducer housing 24. The sealing member 52 prevents blood flow back through the housing.

Figure 15:
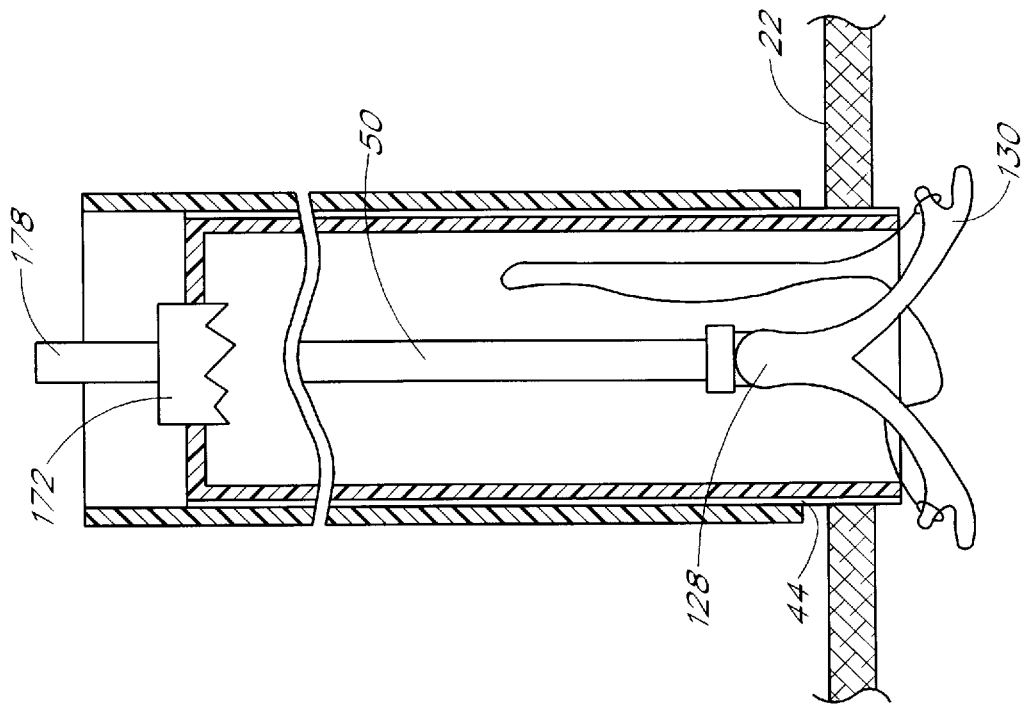
FIG. 15 is a partial cross-sectional view of the embodiment of FIG. 14 illustrating the suture clasp arms in a deployed position.
Figure 14:
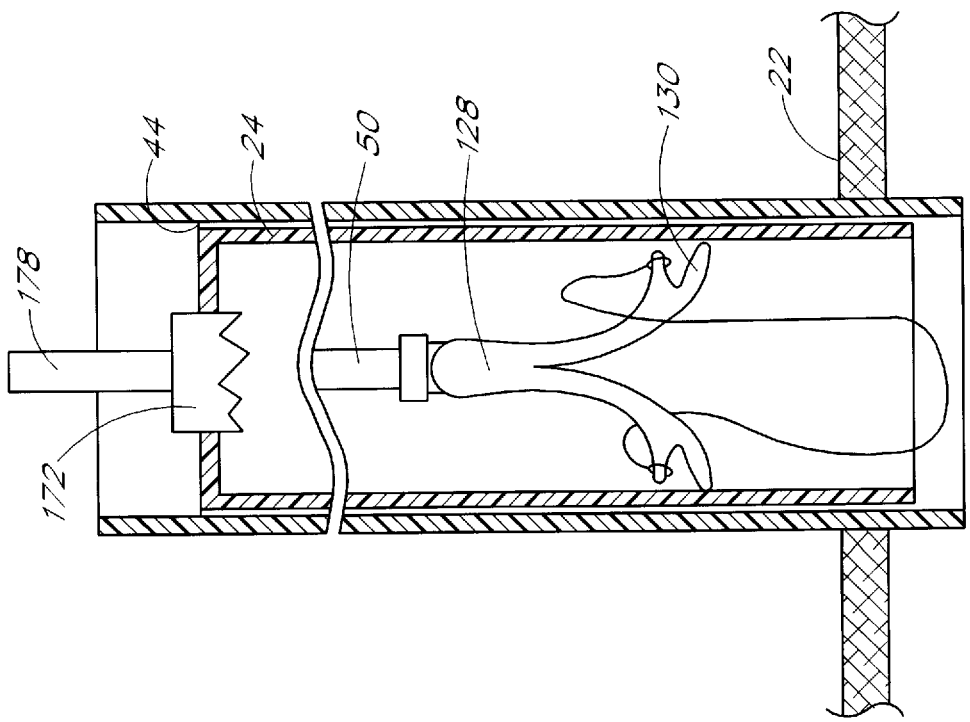
FIG. 14 is a partial cross-sectional view of a further alternate embodiment for deployment of the suture clasp arms.

Still another alternate clasp arm deployment mechanism is illustrated in FIGS. 14 and 15. In this embodiment, a single resilient arm 128 is fixed to the actuating rod 50. The resilient arm is predisposed in a deployed configuration shown in FIG. 15. When the arm is retracted into the housing, the prongs 130 of the arm are elastically deformed inwardly, and when the arm is moved out of the housing by the actuating rod, the prongs expand to the predisposed deployed position. This embodiment is easily adaptable to having four prongs spaced at ninety degrees (90–°). Thus, any configuration and number of prongs can be incorporated into the device depending on the specific needs of the application.

Figure 16:
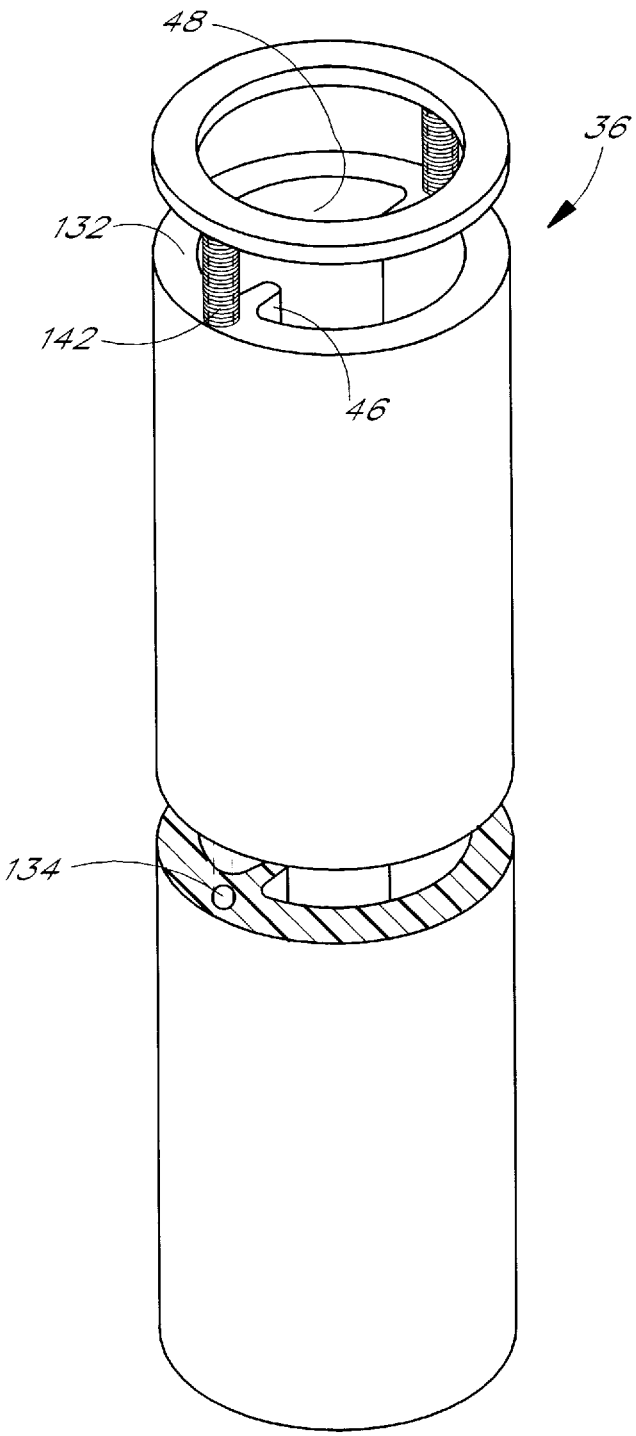
FIG. 16 is a bifurcated perspective view of the suture catch assembly of FIG. 1.

Referring to FIGS. 1 and 16, the preferred embodiment of the suture catch assembly 36 has a generally cylindrical outer tube 132, which, as described, includes a key 46 to mate with the key way groove 44 of the suture introducer housing 24. The inner diameter of the tube is sized to fit over the outer diameter of the suture housing without any interference. This fit does not need to be tight because the suture catch assembly is not inserted into the opening in the vessel. Therefore, there is no need to prevent the flow of blood between the suture housing and the suture catch. The fit between the suture catch assembly and the suture introducer housing does need to be close enough to assure that the suture catch is properly aligned with respect to the suture clasps. Proper alignment is accomplished by a close fit between the key 46 and the key way 44.

The catch assembly comprises a plurality of, preferably two, needle apertures 134 extending through the tube. The apertures are equally spaced around the circumference of the tube. The penetrating mechanism, preferably needles 136, are slidably received in the apertures. The blunt ends 138 of the needles are connected to an activation ring 140, and springs 142 are interposed between the activation ring and the tube. The springs hold the needles in a retracted position so that the needle points are within the tube. With the needles biased in a retracted position by the springs, the suture catch assembly can be handled without the chance of inflicting an unintentional puncture wound. At least one stop 144 is fixed on the inner surface of the tube and engages the top 146 of the suture housing to fix the relative position between the suture housing and the catch assembly, and because the spring can only be compressed a certain distance, the depth of entry of the needles into the vessel is controlled to prevent puncturing the opposite side of the vessel. Further, the fixed relative position between the suture housing and catch assembly assures that the needles pass far enough into the suture catch receiving area to catch the suture. Near the end of the needle is the suture catch 38. The suture catch is an aperture extending to the outer edge on one side of the needle. The aperture is a slot shaped and angled upwardly toward the proximal end of the device. While the needles are being pulled from the vessel, the suture is pulled to the bottom of the suture catch where it cannot come loose.

Figure 17:
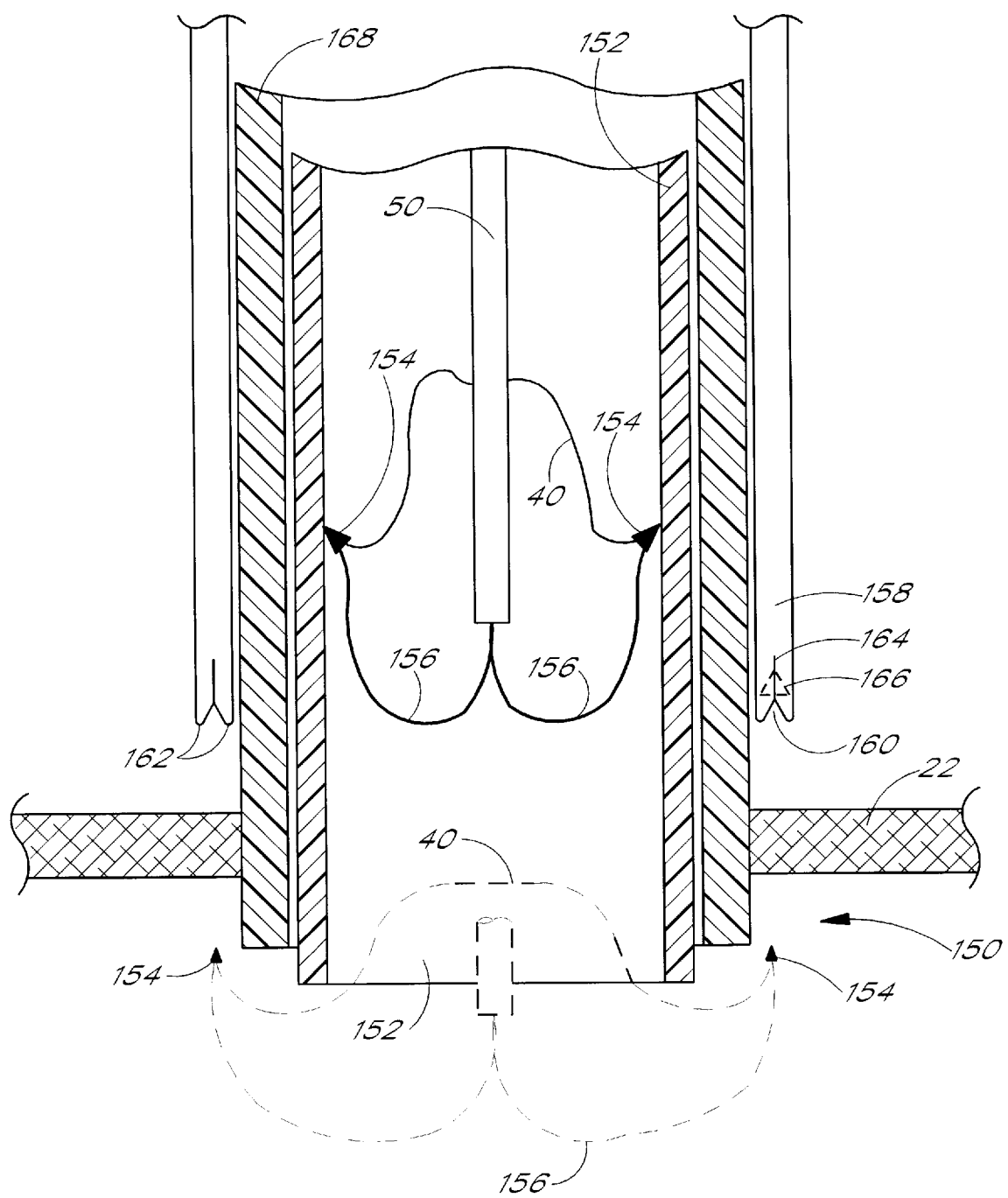
FIG. 17 is a partial cross-sectional view illustrating an alternate embodiment of the suture catch and of the suture clasp arms.
Figure 18:
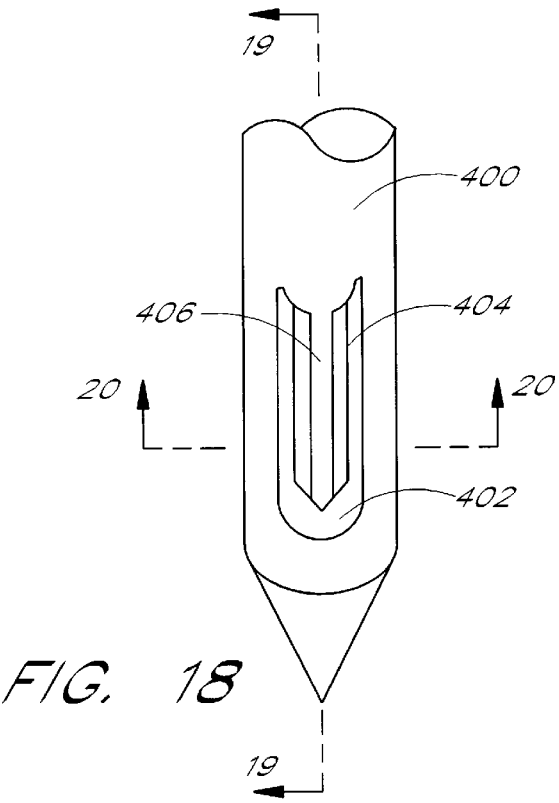
FIG. 18 is a schematic perspective view of a needle tip having an alternate embodiment for catching the suture.
Figure 19:
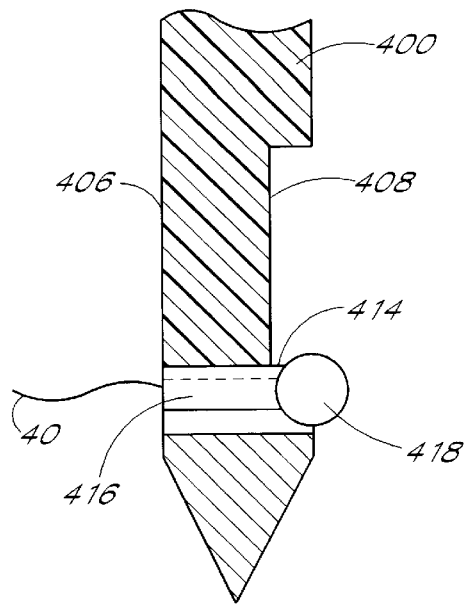
FIG. 19 is a cross-sectional view of the embodiment of FIG. 18 taken along line 19—19 illustrating the position of a suture fitting captured by the suture catch.
Figure 20:
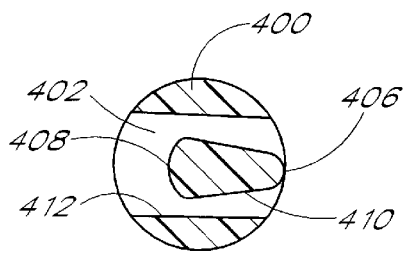
FIG. 20 is a cross-sectional view of the embodiment of FIG. 18 taken along line 20—20.
Figure 21:
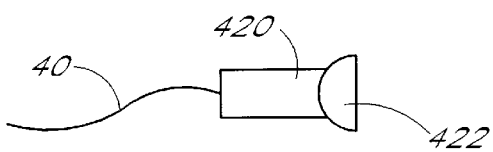
FIG. 21 is a schematic illustration of an alternate embodiment of the suture fitting.
Figure 22:
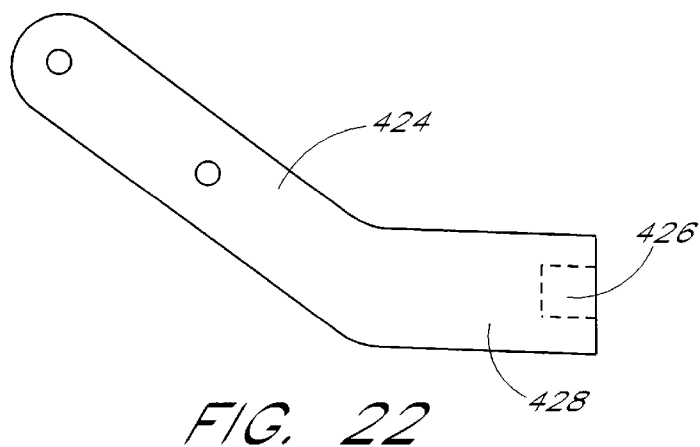
FIG. 22 is a side view of the suture clasp arm used to hold the suture fittings of FIGS. 19 and 21.

In the alternate embodiment of FIG. 17, a penetrating mechanism, generally designated 150, is provided with the suture introducer housing 152. The penetrating mechanism comprises needle points 154 press fit onto arms 156. The end of the arms opposite the needle points are fixed to the actuating rod 50. The arms are made of a resilient material exhibiting shape memory such as NITINOL®, and the arms are at rest in a deployed position shown in dashed lines. When the arms are within the suture housing, they are deformed to fit within the housing. When the actuating rod pushes the needle points beyond the suture housing, the arms return to their at rest position with the needle points beyond the circumference of the housing. The suture 40 is attached to the needle points. The needle points are then pulled by the actuating rod toward the vessel wall 22 thereby penetrating the vessel wall.

The suture catch 158 has a V-shaped notch 160 with rounded tips 162. Further there is a slit 164 extending up from the vertex of the notch 160. The rounded tips prevent the suture catch from inadvertently puncturing the vessel wall. The needle points fit into the notches and cause the notch to open farther along the slit. After the needle points are inside a cavity 166 within the suture catch, the notch collapses to its original shape and traps the needle points inside. The suture catch is then pulled proximally until the press fit between the needle points and the arms is overcome, and the needle points are separated from the arms. The actuation rod is then moved proximally to pull the arms 156 both into the housing.

An alignment mechanism can be provided similar to the key way described above, but in the embodiment shown, the notch is circumferential. Thus, no alignment mechanism is needed, and any number of arms extending form the actuating rod can be provided.

The suture catch can be positioned over an introducer 168 if desired. If the proximal end of the introducer is too large for the suture catch to fit over, the suture catch could be made of a flexible material with a longitudinal slit over its entire length allowing it to be expanded to fit around the diameter of the introducer. The arms would be modified so that the needle points extend beyond the circumference of the introducer.

An alternate embodiment of the suture catch and suture clasp is illustrated in FIGS. 18 through 22. A needle 400 is provided with a slotted opening 402 having a peg 404 extending from the top of the opening through a portion thereof. The peg has a narrow and rounded front peg surface 406 with an identical radial location on the needle as the outer surface of the needle. The back peg surface 408 of the needle is relatively wide, rounded, and located toward the radial center of the needle. The peg sides 410 are flat and angled relative to the walls 412 of the slotted opening 402. The slotted opening receives suture fitting 414 having a shaft 416 connected, preferably by crimping, to the suture and an enlarged termination 418 which is preferably spherical. The alternate suture fitting 420 of FIG. 21 has a half spherical termination 422 with rounded edges. The half spherical termination does not protrude beyond the diameter of the needle. Thus, reducing the trauma to the vessel when the needle is retracted. The shaft in either embodiment has a length short enough not to protrude from the diameter of the needle when the suture fitting is held by the needle. This also reduces trauma to the vessel during retraction.

The suture fitting is held by a modified suture clasp arm 424 having an aperture 426 to receive the shaft of the suture fitting. The wall 428 of the aperture is slowly tapered so that the diameter decreases as the aperture moves inwardly in the arm. This frustoconical shape provides a secure press fit with the suture fitting shaft. Other aperture shapes are possible so long as the press fit is secure and is of a force which can be overcome by the retraction of the arm. The shaft of the suture fittings can also be tapered to better mate with the aperture.

When the suture clasp arm is deployed, the termination engages the peg forcing it to one side allowing the termination to slide against the peg until the termination is past the peg. When the termination slides past the peg, the peg snaps toward its at rest central position thereby capturing the termination and hence the suture. When the suture clasp arm is retracted, the press fit is overcome and the suture fitting is pulled from the arm. When the peg snaps back into its central position, it tends to pull the suture fitting away from the suture clasp arm. This can be utilized to help overcome the press fit. With the suture filling securely held, the needles are retracted, the suture fittings cut from the suture, and the suture tied.

Another alternate embodiment of the suture catch is illustrated in FIGS. 23 and 24. A needle 450 is provided with a slot shaped opening 451 with a U-shaped raised portion 452 in the lower front of the slot. The opening also defines a suture fitting receiving area 454 at the top of the opening for receiving a suture fitting 456 and a suture fitting catch area 458 in the lower back of the slot adjoining the raised portion. The suture fitting has a spherical tip 459, and an arcuate neck 460 which tapers down to a cylindrical shaft 462. The spherical tip is sized to fit through the suture fitting receiving area but not through the U-shaped raised potion. Thus, the raised portion holds the suture fitting in the suture fitting catch area. The raised portion angles toward the back of the needle, so that it becomes larger as it extends farther down the needle.

As shown in FIGS. 25 and 26, another alternate embodiment of the suture clasp arms 464 comprises an upwardly facing key hole shaped opening 466 for holding the suture fitting. The opening faces upwardly, that is in the direction of needle retraction, to aid in the removal of the suture fitting from the suture clasp arm.

In operation, the suture catch is activated to penetrate the tissue to be sutured. The suture clasp arms are deployed directing the suture fitting into the suture fitting receiving area. As the suture catch needle is retracted, the neck of the suture fitting is engaged by the raised portion, and the angled surface of the raised portion pulls the suture fitting farther and farther toward the back of the needle. Thus, the suture fitting is being pulled out of the suture clasp arm as the needle is retracted. If the suture fitting is not completely removed from the suture clasp arm when it contacts the bottom of the opening 451, it is snapped upwardly passed a neck 468 of the key hole opening 466 and out of the suture clasp arm.

The control of the distal and proximal translation of the actuating rod 50 is preferably performed by the three sector, arm actuator assembly, generally designated 170, which is attached to the suture introducer housing 24 (see FIG. 2). Each sector of the arm actuator assembly is substantially identical, and referring to FIGS. 27–30, the arm actuator handle is comprised of three pieces: a button 172, a cylindrical guide 174, and a catch 176.

The button 172 comprises an actuation post 178 extending centrally from a closed end of a cylindrical body 180. The cylindrical body is sized to longitudinally slide in the guide. Three button tabs 182 are spaced equally around the outer surface of the cylindrical body at the end opposite the actuation post 178. Thus, there is one button tab in each sector.

The catch comprises three catch tabs 184 corresponding to the three button tabs, a cylindrical body 186 which is sized to fit rotatably inside the cylindrical body 180 of the button, and a control ring 188 at an end of the cylindrical body for engaging the three button tabs 182. The control ring is at the end of the catch corresponding to the end of the button having the button tabs, and the catch tabs which rotate from sector to sector extend radially from the central ring.

The guide, which is attached at its proximal end to the housing, has three channels 190 and three notches 192, and the guide is open at both ends; so that the button protrudes from the proximal end, and the catch can extend from the opposite (distal) end. There is one channel in each sector with a notch adjacent thereto. The button tabs 182 and the catch tabs 184 are slidable within the channels, each button tab stays in the same channel while each catch tabs is rotated from a channel to a notch and to another channel during operation.

As indicated, the outer diameter of the button is sized to slide inside the guide. Preferably, there is a button gap 194 between the button and the guide. The diameter of the control ring is sized to rotate freely within the guide with minimum clearance, and the catch cylindrical body is sized to rotate and slide longitudinally inside the button cylindrical body with minimum clearance. This leaves a relatively large catch gap 196 between the catch cylindrical body and the guide. Therefore, the length of the catch cylindrical body is preferably long enough so that it is never withdrawn from the button cylindrical body during operation. Because there is a button gap 194 between the button cylindrical body and the guide, the button tabs have a thickness sufficient to extend across the gap 194 and into the channels. Thus, the button tabs also overlap the diameter of the control ring, so that the button tabs can engage the control ring. The bottom surface 195 of the button is contoured to mate with the control ring. The catch tabs have a diameter and thickness so that they slide in the channels and fit into the notches. Preferably, the outer diameter of the guide is the largest diameter thereby assuring adequate clearance for translation of the button and catch tabs.

Figure 27:
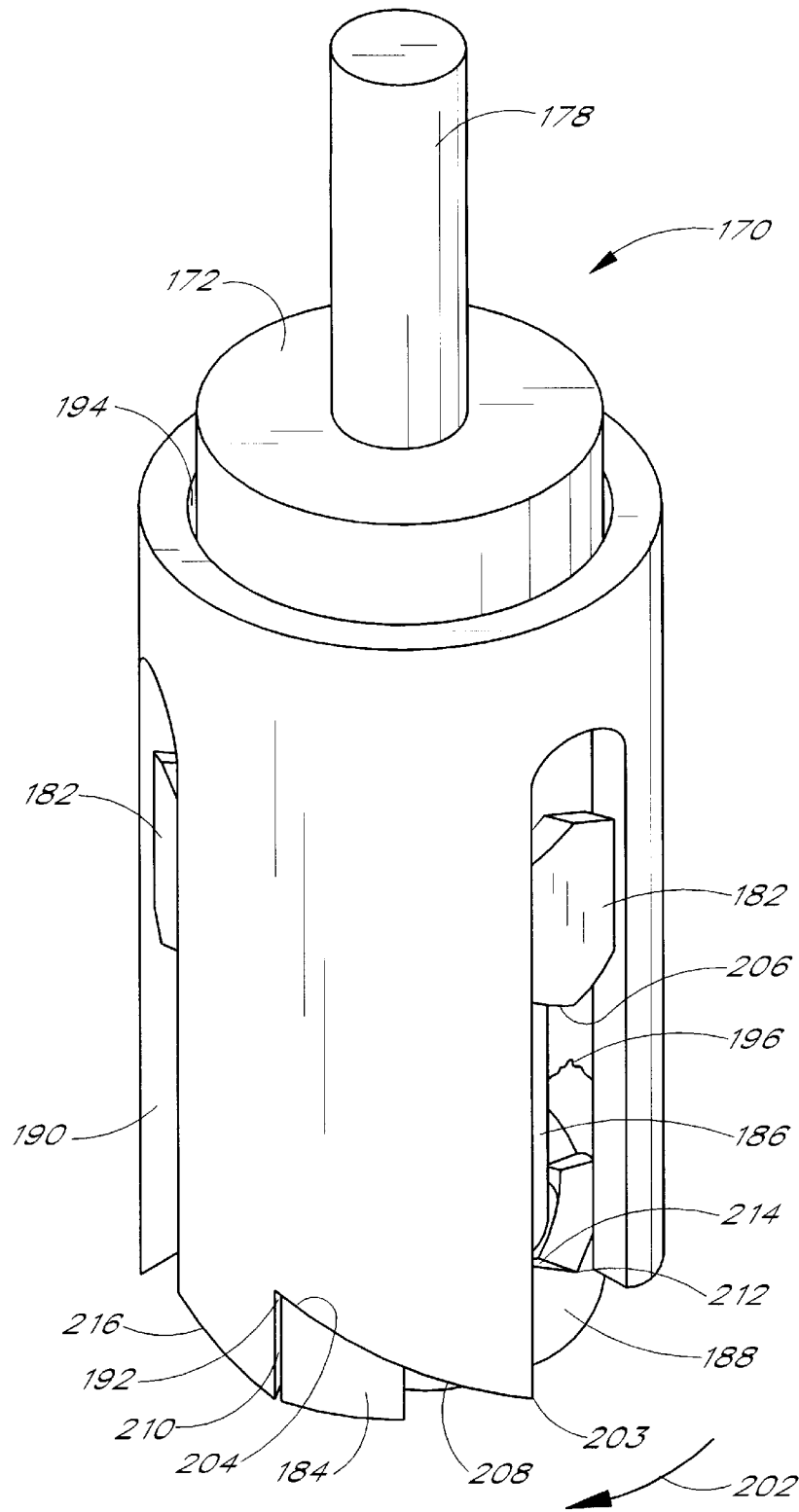
FIG. 27 is a perspective view of a three-sector arm actuator assembly with a catch in a distal position.
Figure 28:
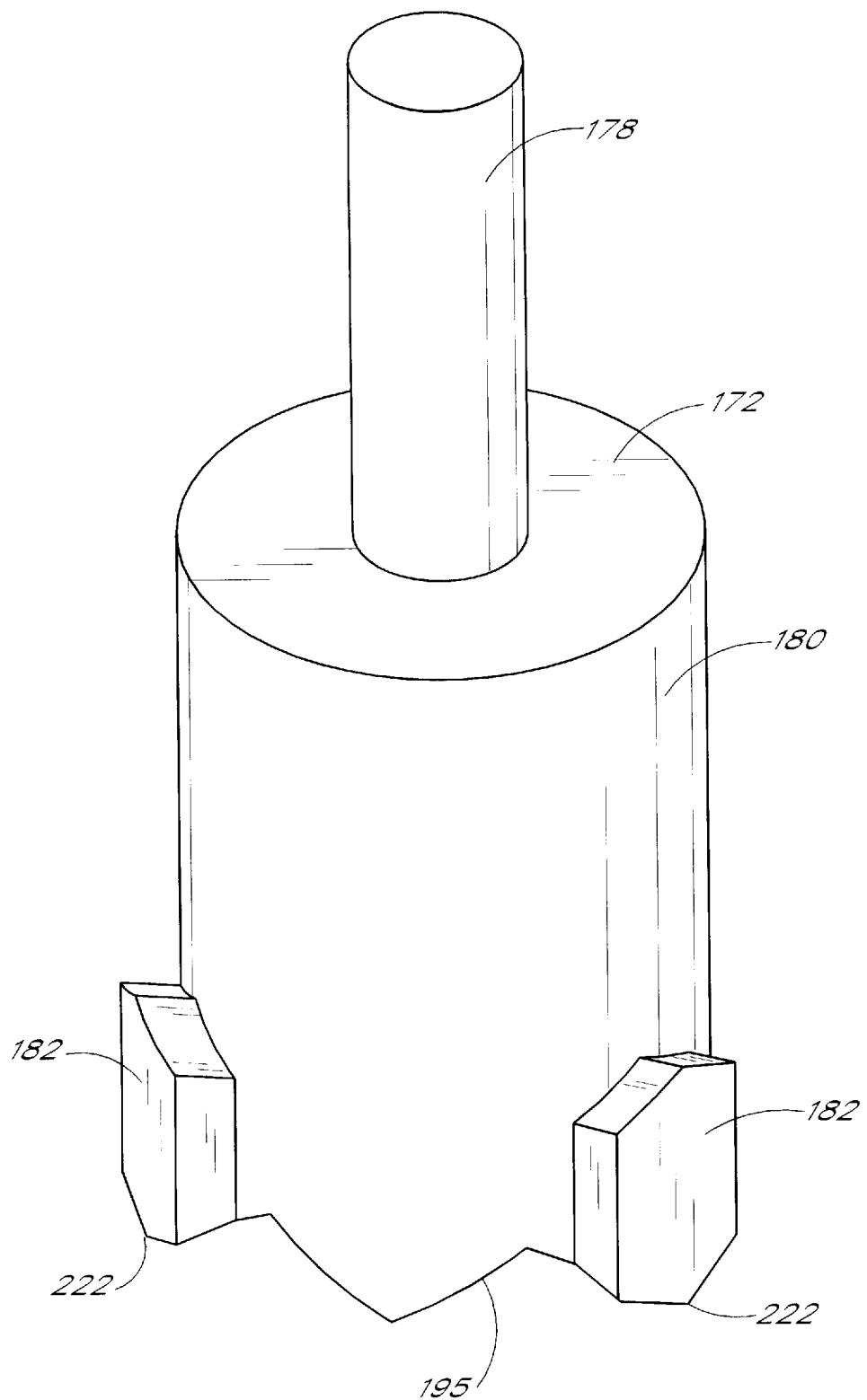
FIG. 28 is a perspective view of a button of the assembly of FIG. 27.
Figure 29:
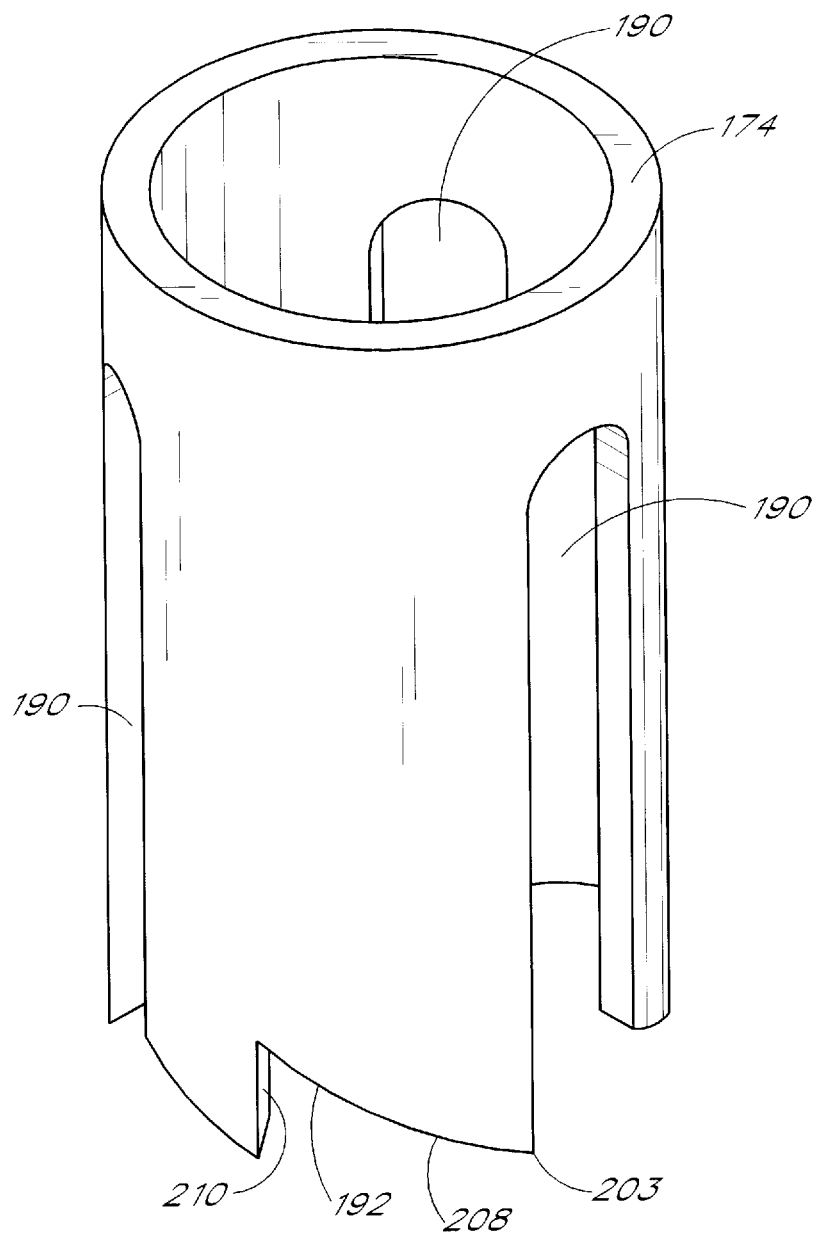
FIG. 29 is a perspective view of a guide of the assembly of FIG. 27.
Figure 30:
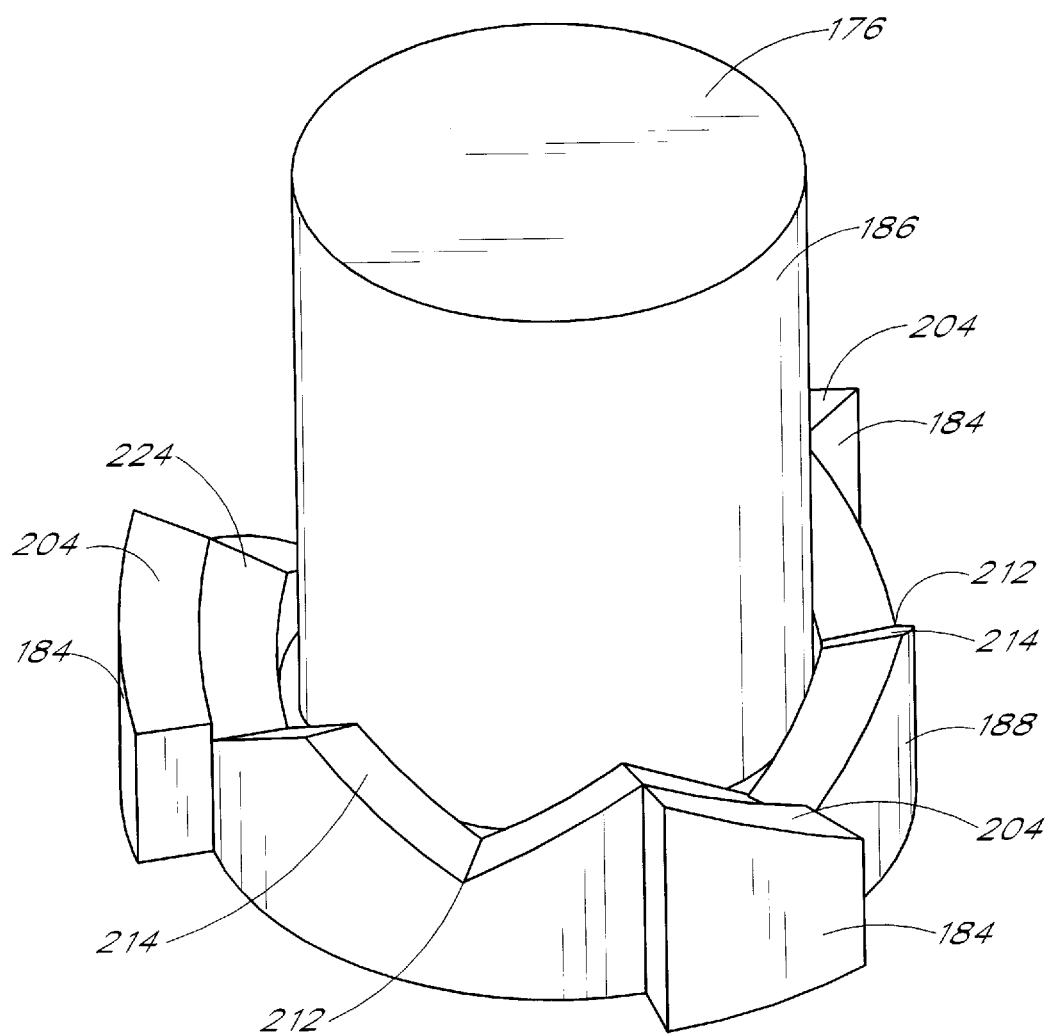
FIG. 30 is a perspective view of the catch of the assembly of FIG. 27.
Figure 31:
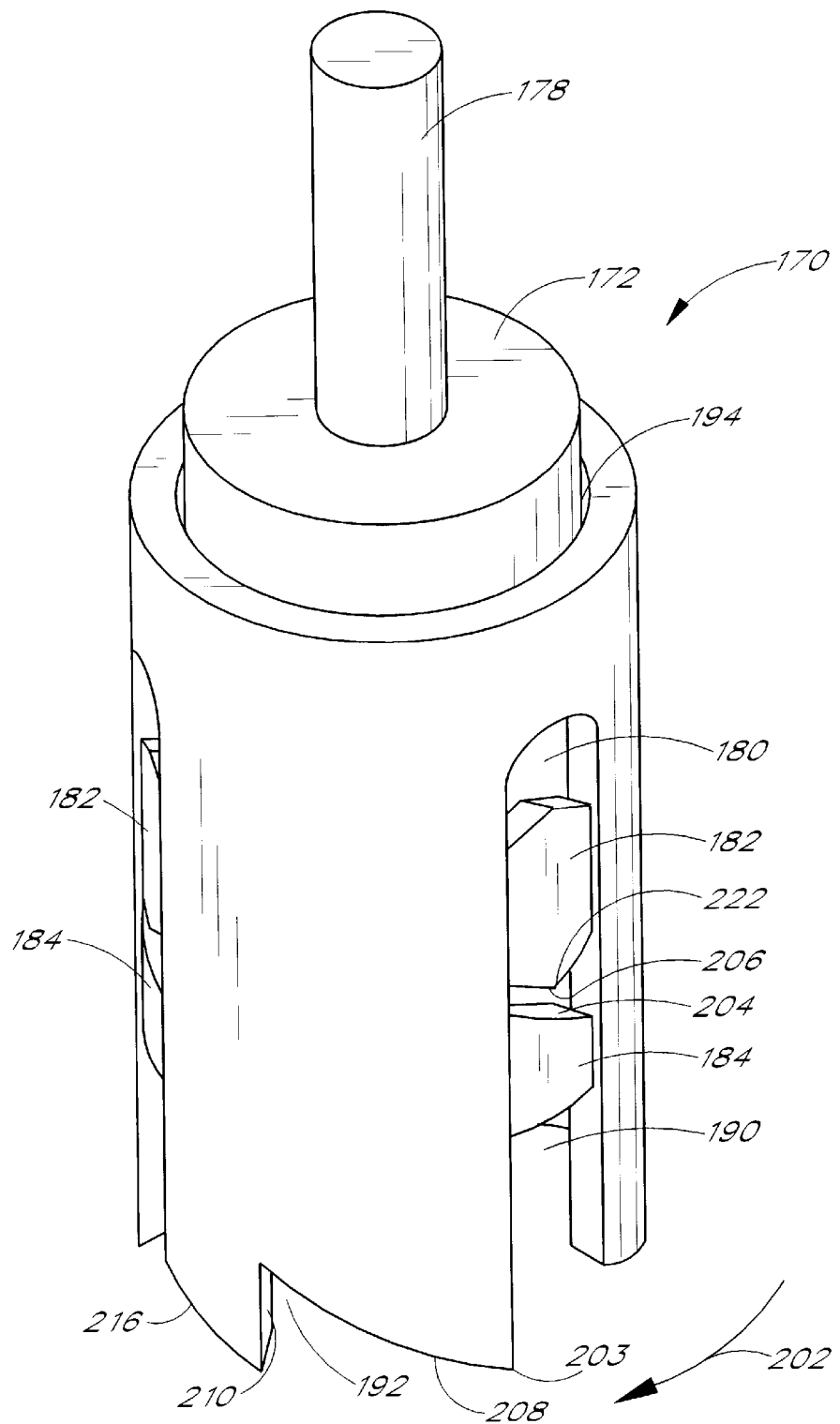
FIG. 31 is a perspective view of the assembly of FIG. 27 with the catch in a proximal position.
Figure 32:
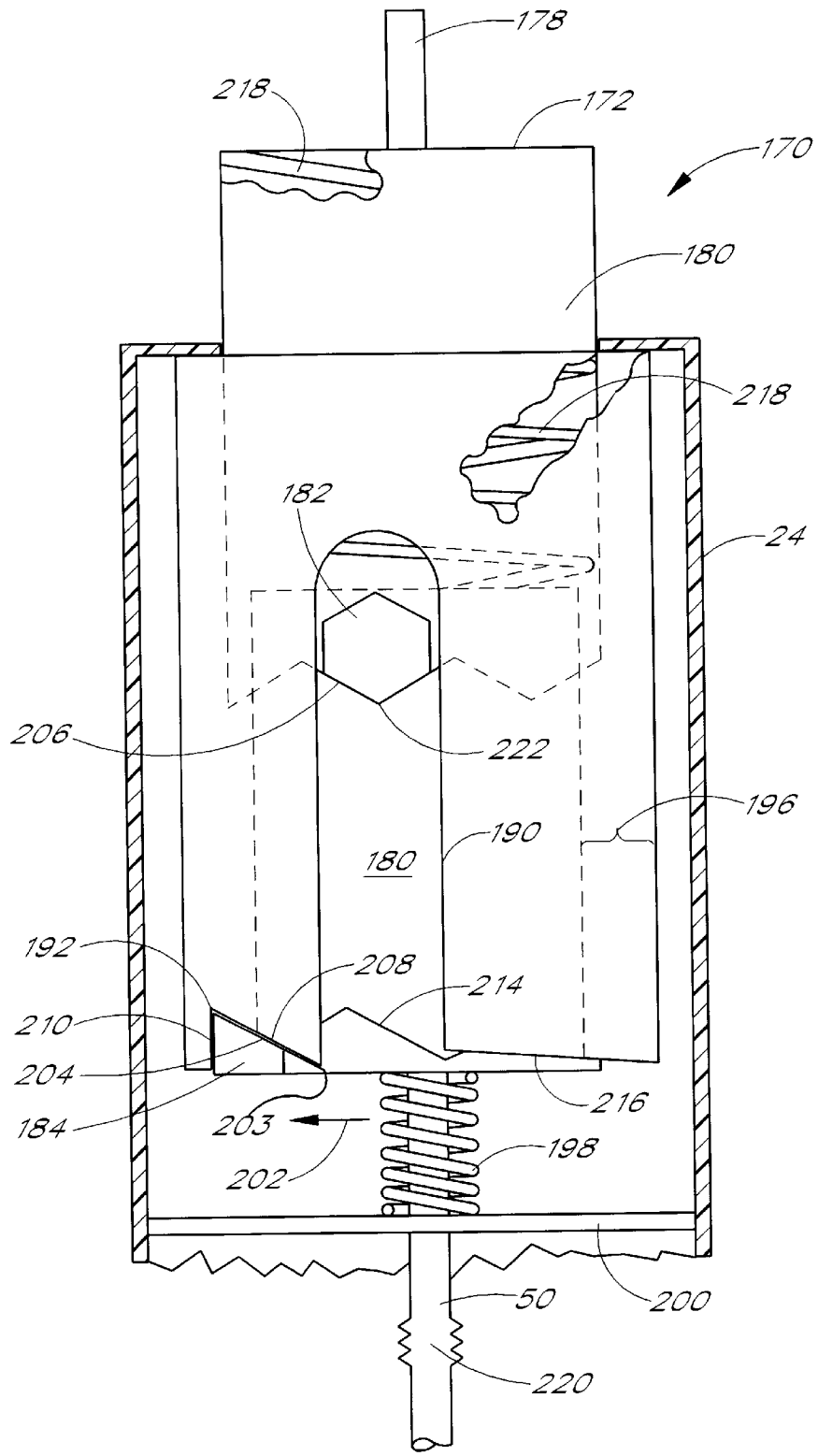
FIG. 32 is a schematic partial cross-sectional view of the assembly of FIG. 27 with the catch in a distal position.

Referring to FIGS. 27, 31, and 32, in operation, the catch starts out in a proximal position with the catch tabs in the channels as shown in FIG. 31. A rotation spring 198 is held in compression between fixed plate 200, which is attached to the housing 24, and the catch. The rotation spring biases the catch in the proximal direction, which corresponds to a retracted suture clasp arm position. The health practitioner presses down on the actuation post of the button causing the button tabs to move distally pressing against the catch tabs and control ring thereby moving the catch tabs distally until the catch tabs are beyond the distal edge 203 of the channels. At this point, the catch rotates in the direction of arrow 202. The rotation is created by the rotation spring pushing a top angled surface 204 of the catch tab against the bottom angled surface 206 of the button tabs. As the catch rotates, it also translates upwardly because of the angled surfaces. This prevents the catch from rotating past the notch. The health practitioner then releases the actuation post allowing the rotation spring to push the catch tabs against the angled notch surface 208 and rotate the catch tabs until they contact the vertical notch stops 210 as illustrated in FIG. 27. In this rotational position, V-shaped depressions 212 on the control ring are aligned with the channels 190 of the guide. When the catch tabs are in the notches, the suture clasp arms are in a deployed position.

To retract the needles, the health practitioner again depresses the actuating post, so that the button tabs engage the V-shaped depressions 212 in the control ring located between the catch tabs. This pushes the catch tabs below the bottom of the guide. The rotation spring pushing upward on the guide causes the slide surface 214 of the V-shaped depression to slide across the bottom surface of the button tab causing the catch tabs to rotate and move upwardly until they engage the angled bottom return surfaces 216 of the guide. After the health practitioner releases the actuation post, the rotation spring continues to force the catch tab to slide over the return surface until the catch tab reaches the channel and the spring forces the catch tab upwardly into the channel thereby retracting the suture clasp arms. As shown in FIG. 32, a button spring 218 can be provided between the catch and the button to return the button to an upward position after it is released. If the button spring is used, the button tabs contact the tops of the channels preventing the button from coming off the assembly.

The suture clasp arms are completely deployed when the catch tab is in the notch against the notch stop. For the operation of the actuator assembly, the catch tab is pushed below this level several times. To prevent the arms from going past a fully deployed position, a resilient member 220 is placed in the actuating rod 50. Once the suture clasp arms reach the fully deployed position, their further motion is restricted as described above. As the catch tab is pushed below the position corresponding to the fully deployed position, the resilient member 220 is compressed allowing the catch tab to be moved the rest of the way below the bottom surface of the guide so that it can rotate to the next position. This prevents damage to the spreader, bending the actuating rod, and risk of injury to the vessel.

To allow the catch to begin rotating after it clears the bottom of the channel or the bottom of the vertical notch stop. The vertex 222 of the button tab is not aligned with the bottom of the V-shaped depression when the V-shaped depression is aligned with the channel. The vertex of the depressions 212 is positioned to a side of the vertex of the button tab in the rotational direction, so that the catch is allowed to rotate until it is underneath the shallow end of the return surface 216 of the guide. Similarly, when the catch tab is inside the channel, the angled surfaces 224 of the control ring corresponding to the catch tab continue past the catch tabs to again allow initial rotation of the catch until the catch tab is beneath the shallow end of the notch surface. Thus, the catch tab can rotate underneath the shallow end of the notch before the button tabs contact the lowest point of the control ring surfaces 224 and rotation is restricted. When the rotation is restricted, the actuation post is released raising the button tab out of the way, and the catch can complete its rotation.

FIGS. 33 and 34 illustrate the preferred application of the present invention. An incision 230 is made in the upper thigh 234 of a patient 232. Another incision is made inwardly from the first incision to create the opening 26 in the femoral artery 238. The opening 26 in the artery provides access inside the arterial vessel, and the introducer 168 is inserted into the incision. Other instruments, such as catheters, are inserted into the introducer to perform various procedures in the body. After the required procedures are complete, the above described difficulty is encountered with closing the opening 26 in the arterial wall.

The operation of the device is illustrated in sequence by FIGS. 1, and 34 through 37. Instead of removing the introducer and applying pressure, the introducer is left in place, and the suture introducer housing 24 is inserted into the introducer and introduced into the artery as shown in FIGS. 34 and 35. The actuation post is then depressed, as illustrated by arrow 240 in FIG. 36 to deploy the suture clasp arms 28, 30 outwardly as illustrated by arrows 242 so that portions, preferably the ends, are positioned on opposite sides of the opening 26 with the suture extending transverse to the flow of blood. The introducer is then removed leaving the suture introducer housing with the suture clasp arms deployed inside the artery. The opening 26 in the vessel closes around the housing after the introducer is removed. Referring temporarily to FIG. 39, the suture introducer housing is then oriented so that the arms extend transversely to the flow of blood through the vessel which is illustrated by arrow 244. The suture catch assembly 36 is then inserted over the housing 24 and the stop 144 is brought into contact with the top 146 of the housing 24 as shown in FIG. 1. A health practitioner depress the activation ring 140 as illustrated by arrows 246 pushing the needles 136 through the vessel wall 22 and puncturing holes 248 in the vessel. The suture catch 38 catches the suture, and the suture catch assembly is pulled proximally as illustrated by arrows 250. The needles can be retracted inside the suture catch assembly or left deployed. The suture is cut from the suture catch and pulled tight to remove it from the housing. The suture clasp arms are retracted by depressing the actuation post again, and the suture is pulled tight simultaneously with the housing being pulled out of the artery. Alternatively, the length of the actuation post is set to correspond with the height of the depressed activation ring. Thus, when the activation ring is depressed, the actuation post is simultaneously depressed for the second time thereby retracting the arms simultaneously with pulling the suture catch assembly proximally. With the suture catch removed the pattern of holes shown in FIGS. 39 and 40 is left. As stated the suture closes the artery transverse to the flow of blood. This is the most efficient direction to close the opening. If additional arms are utilized, it is preferred that they make additional holes around the circumference of the opening as shown in dashed lines, so that sutures again pull the opening closed in a direction transverse to the flow of blood.

The device could be similarly used to close a patent ductus arteriosus, a patent foramen ovale, a heart defect, a puncture wound in the skin, and other tissues requiring suturing.

Figure 41:
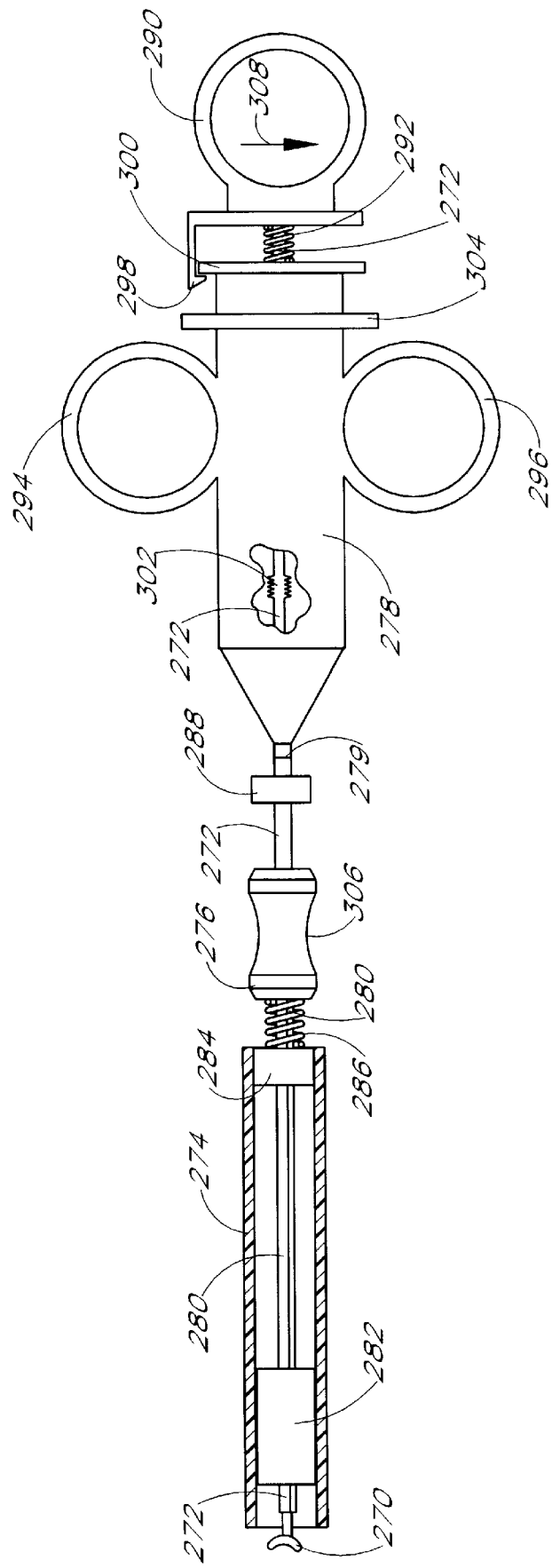
FIG. 41 is a schematic partial cross-sectional view of an alternate embodiment of the suturing device having a detachable arm deployment handle.

An alternate embodiment of the suturing device is shown in FIG. 41. The device comprises a pair of suture clasp arms 270 attached to the end of and actuating rod 272 in accordance with one of the above described embodiments. The actuating rod extends through a needle cover 274 and slidably through a needle actuator 276 to a suture arm deployment handle 278. Near the deployment handle the actuating rod has a severable junction 279. The junction is threaded or snap fit allowing the actuating rod to be quickly separated and joined thereby quickly removing or attaching the handle from the remainder of the device. The actuation rod can, in the alternative, have a junction where it enters the needle cover 274. Needles 280 are held near their distal ends by a needle guide 282 and pass through a stop 284 that limits the deployment distance of the needles. The needles fixably attaching to the needle actuator. A spring 286 is interposed between the stop and the needle actuator to bias the needles in a retracted position. A second stop 288 is fixed to the actuating rod on the opposite side of the needle actuator to prevent the needles from being pulled out of the needle guide. The actuating rod terminates at a thumb ring 290 separated from the distal end of the suture arm deployment handle by a thumb ring spring 292 which biases the thumb ring in a proximal position which corresponds to a retracted position of the suture clasp. The handle also comprises two finger rings 294, 296 on opposite sides of the handle allowing an operator to smoothly overcome the force of the thumb ring spring 292.

In operation, the distal portion of the device, from the needle cover 274 to the suture clasp arms, is inserted into the introducer with the handle detached. The introducer is removed and the handle is attached to the device by connecting the actuating rod. The thumb ring is pushed distally to deploy the suture clasp arms. A clip 298 hooks onto a clip ring 300 to lock the suture clasp arms in the deployed position. The actuating rod includes a resilient member 302 (shown schematically), which functions, as described in the previous embodiments, to prevent the suture clasp arms from moving past their deployed position. The resilient member can simply comprise a spring, or a spring housing can be provided on one part of the actuation rod to receive a spring and a slidable plunger therein. The plunger, which is provided on the opposite part, slides to a maximum distal position defined by the spring housing and is biased in that position by the spring. When the suture clasp arms reach a deployed position, the plunger is then forced into the housing compressing the spring and allowing the upper portion of the actuation rod to travel distally without forcing the suture clasp arms past a deployed position or bending the actuation rod. A thumb ring stop 304 prevents the thumb ring from being pushed beyond a point for which the resilient member 302 could compensate.

With the suture clasp arms deployed, the health practitioner grasps the needle actuator, which has a central curved indented surface 306 to make it easy to grasp, and pushes the needle actuator distally. The needles are pushed into the vessel and catch the suture as described in one of the above embodiments. The stop 284 prevents the needles from penetrating too far and damaging the vessel. The spring 286 pushes the needles back to a retracted position when the needle actuator is released.

With the suture held by the needles, the thumb ring is pushed in a direction transverse to the length of the actuating rod and away from the clip 298 as illustrated by arrow 308 to release the clip and retract the suture clasp arms. The entire device is retracted, the suture cut from the needles, and the suture tied to close the opening. Because the handle is detachable, the handle could be used in conjunction with the above described embodiments. In such a case, the arm actuator assembly would be removed, and the actuating rod would extend through the top of the housing. The end of the actuating rod would be modified to connect to the handle.

Thus, various embodiments of a suturing device are disclosed which utilize remotely operable suture clasp mechanisms and suture catch mechanisms to more efficiently establish blood clots on the femoral artery and to suture tissue which would previously have been impossible or undesirable to suture. While embodiments and applications of this invention have been shown and described, it is apparent to those skilled in the art that many more modifications are possible without departing from the inventive concepts herein. It is, therefore, to be understood that within the scope of the appended claims, this invention may be practiced otherwise than as specifically described.

What is claimed is:

1. A suturing device for suturing an opening in a vessel wall comprising:

a housing;

an actuator supported within the housing;

at least one suture clasp for holding a suture wherein the suture clasp is operatively coupled to the actuator and comprises a pair of tips each having an outside edge defining an indentation adapted to receive a suture and engage a knot or bead on a suture whereby the suture is held by the suture clasps; and at least one suture catch supported by the housing and operatively positioned relative to the suture clasp to capture a suture held by the suture clasp.

2. The suturing device according to claim 1 further comprising at least a resilient element attached to each of the tips.

3. A suturing device for suturing an opening in a vessel wall comprising:

a housing;

an actuator supported within the housing;

at least one suture clasp for holding a suture, wherein the suture clasp is operatively coupled to the actuator, and at least one suture catch supported by the housing and operatively positioned relative to the suture clasp to capture a suture held by the suture clasp, wherein the suture catch comprises a needle having an angled slot.

4. A suturing device for suturing an opening in a vessel wall comprising:

a housing;

an actuator supported within the housing:

at least one suture clasp for holding a suture wherein the suture clasp is operatively coupled to the actuator;

at least one suture catch supported by the housing and operatively positioned relative to the suture clasp to engage the suture clasp;

a tube having an aperture with the suture clasp deployably disposed therein and an outer surface with a key way; and a suture catch assembly having at least one suture catch operatively positioned relative to the suture clasp and a key to engage the key way and align the tube with the suture catch assembly.

5. A suturing device for suturing an opening in a vessel wall comprising:

a housing;

an actuator supported within the housing;

at least one suture clasp for holding a suture, wherein the suture clasp is operatively coupled to the actuator and comprises an arm defining an aperture for receiving a suture fitting; and at least one suture catch supported by the housing and operatively positioned relative to the suture clasp to capture the suture fitting, wherein the suture catch comprises a needle defining a slot having top, a peg inside the slot and extending downwardly from the top, and the peg being movable to receive a suture fitting.

6. A suturing device for suturing an opening in a vessel wall comprising:

a housing:

a plurality of arms attached to the housing extending in a plurality of directions, each arm having a suture clasp for holding at least one suture;

a penetrating mechanism deployably attached to the housing and operatively positioned relative to the suture clasps to penetrate biological tissue with at least one suture;

a suture introducer housing having the arms deployable disposed therein; and a suture catch assembly having at least one suture catch and an aperture therethrough adapted to receive the introducer housing, the suture catch assembly deployably positioned relative to the suture clasps to capture a suture held by the suture clasps.

7. The suturing device according to claim 6 wherein the penetrating mechanism comprises at least one needle, the suture catch comprises a slot in the needle, and the at least one needle is slidably held by the catch assembly.

8. The suturing device according to claim 7 wherein the suture catch assembly further comprises an activation ring attached to the at least one needle.

9. The suturing device according to claim 8 wherein the activation ring has a stop to control depth of entry of the suture catch.

10. A suturing device for suturing an opening in a vessel wall comprising:

a housing:

a plurality of arms attached to the housing and extending in a plurality of directions, each arm having a suture clasp for holding at least one suture;

a penetrating mechanism deployably attached to the housing and operatively positioned relative to the suture clasps to penetrate biological tissue with at least one suture;

a cylindrical suture introducer housing with an aperture therethrough and wherein the arms have a first retracted position inside the aperture and a second deployed position outside the aperture; and a spreader located in the aperture of the housing, extending across a diameter line of the housing, and being substantially perpendicular to the longitudinal axis of the tube.

11. The suturing device according to claim 10 wherein the spreader comprises a substantially triangular bar.

12. The suturing device according to claim 10 wherein the spreader comprises a cam pin.

13. A suturing device for suturing an opening in a vessel wall comprising:

a housing;

a plurality of arms attached to the housing and extending in a plurality of directions each arm having a suture clasp for holding at least one suture;

a penetrating mechanism deployably attached to the housing and operatively positioned relative to the suture clasps to penetrate biological tissue with at least one suture; and means for aligning the arms and the penetrating mechanism, and wherein the arms comprise an upper lever arm and a lower pivot arm with the suture clasp thereon.

14. The suturing device according to claim 13 wherein the aligning means comprises a key and a key way.

15. The suturing device according to claim 14 wherein the arm actuator assembly comprises three substantially identical sectors.

16. The suturing device according to claim 14 further comprising:

a suture catch assembly having an activation ring; and wherein the arm actuator assembly comprises an actuation post having a height corresponding to a depressed height of the activation ring such that the actuation post is depressed simultaneously with the activation ring.

17. A suturing device for suturing an opening in a vessel wall comprising:

a housing;

a plurality of arms attached to the housing and extending in a plurality of directions each arm having a suture clasp for holding at least one suture;

a penetrating mechanism deployably attached to the housing operatively positioned relative to the suture clasps to penetrate biological tissue with at least one suture;

a suture introducer housing having the arms deployably housed therein;

an actuating rod having a proximal end and having a distal end attached to the arms; and an arm actuator assembly attached to the proximal end of the actuating rod for deploying the arms.

18. A suturing device for suturing an opening in a vessel wall comprising:

a housing;

a plurality of arms attached to the housing and extending in a plurality of directions, each arm having a suture clasp for holding at least one suture;

a penetrating mechanism deployably attached to the housing and operatively positioned relative to the suture clasps to penetrate biological tissue with at least one suture;

an actuating rod having a proximal end and a distal end attached to the arms; and a detachable arm deployment handle removably attached to the proximal end of the actuating rod.

19. A method of suturing a vessel comprising:

holding a suture with at least one suture clasp;

introducing at least a portion of the suture clasp and ends of the suture into an internal passage way of a vessel through an opening in a wall of the vessel;

piercing the vessel wall with a suture catch;

catching the suture with the suture catch;

penetrating a vessel wall with the suture, the step of penetrating comprising retracting the suture catch from the vessel wall; and tying the suture.

20. A method of suturing a vessel comprising:

holding a suture with at least one suture clasp;

introducing at least a portion of the suture clasp and ends of the suture into an internal passage way of a vessel through an opening in a wall of the vessel;

penetrating a vessel wall with the suture;

introducing a suture introducer housing into an opening in a vessel wall;

introducing the suture into the internal passage way of the vessel through the housing;

positioning the suture beyond an outer diameter of the housing; and tying the suture;

wherein penetrating the vessel walls with the suture comprises penetrating the vessel wall outside the outer diameter of the housing.

21. The method according to claim 20 further comprising removing the housing from the opening, and thereafter, tying the suture.

22. The method according to claim 20 wherein positioning the suture comprises positioning the suture with portions of the suture on opposite sides of the opening and the suture extending in a direction transverse to the flow of blood.

23. A method of suturing a vessel comprising:

holding a suture with at least one suture clasp;

introducing at least a portion of the suture clasp and ends of the suture into an internal passage way of a vessel through an opening in a vessel;

penetrating a vessel wall with the suture;

introducing a suture introducer housing through an introducer in the passage way of a vessel;

introducing the suture into the internal passage way of the vessel through the housing;

deploying the suture clasps beyond the outer diameter of the tube; and tying the suture.

24. The method according to claim 23 further comprising:

removing the introducer;

placing a suture catch assembly having an aperture and a suture catch over the outside of the housing;

piercing the vessel wall with the suture catch;

catching the suture; and wherein penetrating the vessel wall with the suture comprises retracting the suture catch from the vessel wall with the suture caught therein.

25. The method according to claim 24 further comprising:

pushing the suture catch assembly over the housing up to the vessel wall.

26. The method according to claim 23 further comprising placing a suture catch assembly having an aperture, a longitudinal slit, and a suture catch over the outside of the introducer.

27. A method of suturing a vessel comprising:

holding a suture with at least one suture clasp;

introducing at least a portion of the suture clasp and ends of the suture into an internal passage way of a vessel through an opening in a vessel;

penetrating a vessel wall with the suture;

orienting the suture perpendicular to the direction of blood flow in the vessel; and tying the suture.

28. A method of suturing a vessel comprising:

holding a suture with at least one suture clasp, wherein the suture clasps are positioned on the end of suture arms and further comprising attaching an arm deployment handle to actuating rod;

introducing at least a portion of the suture clasp and ends of the suture into an internal passage way of a vessel through an opening in a vessel;

penetrating a vessel wall with the suture; and tying the suture.

* * * * *